United States Patent [19]
Peters-Golden et al.

[11] Patent Number: 5,909,734
[45] Date of Patent: Jun. 8, 1999

[54] ADMINISTRATION OF PRODUCTS OF THE 5-LIPOXYGENASE METABOLIC PATHWAY TO ENHANCE ANTIMICROBIAL DEFENSE

[75] Inventors: Marc Peters-Golden; Theodore Standiford, both of Ann Arbor, Mich.

[73] Assignee: Regents of the University of Michigan, Ann Arbor, Mich.

[21] Appl. No.: 08/757,136

[22] Filed: Dec. 3, 1996

[51] Int. Cl.$^6$ .............................. A61B 19/00; A61K 7/04
[52] U.S. Cl. ......................... 128/898; 514/826; 514/888
[58] Field of Search .......................... 128/898; 514/826, 514/888

[56] References Cited

U.S. PATENT DOCUMENTS

| | | | |
|---|---|---|---|
| 5,145,861 | 9/1992 | Ducep et al. | 514/381 |
| 5,674,483 | 10/1997 | Tu et al. | 424/85.2 |

OTHER PUBLICATIONS

M. Lohmann–Matthes et al., "Pulmonary Macrophages," *Eur. Respir. J.* 7:1678–1689 (1994).

J. Langermans et al., "Antimicrobial Functions of Mononuclear Phagocytes," *J. Immunol. Methods* 174:185–194 (1994).

S. Nelson et al., "Pathology of Pneunomia," *Clin. Chest Med.* 16(1):1–12 (1995).

E. Goetzl et al., "Specificity of Expression and Effects of Eicosanoid Mediators in Normal Physiology and Human Diseases," *FASEB J* 9:1051–1058 (1995).

J. Woods et al., "5–Lipoxygenase Is Located In the Euchromatin of the Nucleus in Resting Human Alveolar Macrophages and Translocates to the Nuclear Envelope Upon Cell Activation," *J. Clin. Invest.* 95:2035–2040 (1995).

M. Peters–Golden et al., "Alterations In the Pattern of Arachidonate Metabolism Accompany Rat Macrophage Differentiation In the Lung," *J. Immunol.* 144(1):263–270 (1990).

T. Martin et al., Relative Contribution of Leukotriene $B_4$ to the Neutrophil Chemotactic Activity Produced by the Resident Human Alveolar Macrophage, *J. Clin. Invest.* 80:1114–1124 (1989).

T. Martin et al., Effects of leukotriene $B_4$ in the Human Lung. Recruitment of Neutrophils Into the Alveolar Spaces Without a Change in Protein Permeability, *J. Clin. Invest.* 84(5):1609–1619.

T. Demitsu et al., "Phagocytosis and Bactericidal Action of Mouse Peritoneal Macrophages Treated With Leukotriene $B_4$," *Int. J. Immunopharmac.* 11(7):801–808 (1989).

P. Marder et al., "Blockade of Human Neutrophil Activation by 2–[2–Propyl–3[3–[2[Ethyl–4–(4–Fluorophenly)–5–Hydroxyphenoxy]Propoxy]Phenoxy]Benzioc Acid (LY293111), A Novel Leukotriene $B_4$ Receptor Antagonist," *Biochem. Pharmacol.* 49(11):1683–1690 (1995).

C. Serhan et al., "Leukotriene $B_4$ Is A Complete Secretagogue In Human Neutrophils: A Kinetic Analysis," *Biochem. Biophys. Res. Commun.* 107(3):1006–1012 (1982).

J. Wijkander et al., "5–Lipoxygenase Products Modulate the Activity of the 85–kDa Phospholipase $A_2$ in Human Neutrophils," *J. Biol. Chem.* 270(44):26543–26549 (1995).

J. O'Flaherty et al., "Mechanisms Involved In the Bidirectional Effects of Protien Kinase C Activators on Neutrophil Responses to Leukotriene $B_4$," *J. Immunol.* 144(5):1909–1913 (1990).

R. Strieter et al., "Cycotine–induced Neutrophil–derived Interlukin–8," *Am. J. Pathol.* 141(2):397–407 (1992).

R. Bray and Z. Brahmi, "Role of Lipoxygenation in Human Natural Killer Cell Activation," *J. Immunol.* 136(5):1783–1790 (1986).

J. Rhodes et al., "Macrophage $Fc\gamma_{2b}$ Receptor Expression and Receptor–Mediated Phospholipase Activity: Regulation By Endogenous Eicosanoids," *Eur. J. Immunol.* 15:222–227 (1985).

M. Peppelenbosch et al., "Epidermal Growth Factor–Induced Actin Remodeling Is Regulated by 5–Lipoxygenase and Cyclooxygenase Products," *Cell* 74:565–575 (1993).

A. Buret et al., Effector Mechanisms of Intestinally Induced Immunity To Pseudomonas Aeruginosa in the Rat Lung: Role of Neutrophils and Leukotriene $B_4$, *Infect. Immun.* 61(2):671–679 (1993).

H. Hopkins et al., "Neutrophil Chemotactic Factors in Bacterial Pneumonia," *Chest* 95(5):1021–1027 (1989).

R. Moqbel et al., "Enhancement of Neutrophil– and Eosinophil–mediated Complement–dependent Killing of Schistosomula of Schistosoma Mansoni In Vitro By Leukotriene $B_4$," *Clin. Exp. Immunol.* 52:519–527 (1983).

M. Balter et al., "Different Patterns of Arachidonate Metablism In Autologous Human Blood Monocytes and Alveolar Macrophages," *J. Immunol.* 142(2):602–608 (1989).

T.G. Brock et al., "Localization of 5–Lipoxygenase to the Nucleus of Unstimulated Rat Basophilic Leukemia Cells," *J. Biol. Chem.* 269(46):22059–22066 (1994).

M. Balter et al., "Multiple defects In Arachidonate Metabolism In Alveolar Macrophages From Young Asymptomatic Smokers," *J. Lab.Clin. Med.* 114:662–673 (1989).

M. Coffey et al., "5–Lipoxygenase Metabolism In Alveolar From Subjects Infected With thte Human Immunodeficiency Virus," *J. Immunol.* 157:393–399 (1996).

M.J. Coffey et al., "Reduced 5–Lipoxygenase Metabolism of Arachidonic Acid in Macrophages Rrom 1, 25–Dihydroxyvitamin $D_3$–Deficient Rats," *Prostaglandins.* 48:313–329 (1994).

(List continued on next page.)

*Primary Examiner*—David J. Isabella
*Attorney, Agent, or Firm*—Medlen & Carroll, LLP

[57] ABSTRACT

The use of leukotrienes and other products of the 5-lipoxygenase pathway to enhance bacterial defense and treat infections is described. The products are especially useful when administered to the lungs for the treatment of pneumonia and other lower respiratory tract infections. The products may be administered for treatment or prophylactic purposes and may be administered concomitantly with antibiotics to combat infection.

14 Claims, 7 Drawing Sheets

OTHER PUBLICATIONS

J. Goulet et al., "Altered Inflammatory Responses In Leukotriene–Deficient Mice," *Proc. Natl. Acad. Sci. USA* 91:12852–12856 (1994).

X. Chen et al., "Role of Leukotrienes Revealed By Targeted Disruption of the 5–Lipoxygenase Gene," *Nature* 372:179–182 (1994).

McColm et al., "Evaluation of Ceftazidime In Experimental Klebsiela Pneumoniae Pneumonia: Comparison With Other Antibiotics qand Measurements of Its Penetration Into Respiratory Tissues and Secretions," *J. Antimicrob. Chemother.* 18:599–608 (1986).

M. Greenberger et al., "Neutralization of IL–10 Increases Survival In a Murine Model of Klebsiella Pneumonia," *J. Immunol.* 155:722–729 (1995).

M. Schneemann et al., "Nitric Oxide Synthase Is Not a Constituent of the Antimicrobial Armature of Human Mononuclear Phagocytes," *J. Infect. Dis.* 167:1358–1363 (1993).

J. Wilborn et al., "Constitutive Activation of 5–Lipoxygenase in the Lungs of Patients with Idiopathic Pulmonary Fibrosis," *J. Clin. Invest.* 97(8):1827–1836 (1996).

L. Laichalk et al., "Interleukin–10 Inhibits Neutrophil Phagocytic and Bactericidal Activity,"*FEMS Immunol. Med. Microbiol.* 658:1–7 (1996).

R. Crowell et al., "Hyperoxic Suppression of Fc–γ Receptor–mediated Phagocytosis By Isolated Murine Pulmonary Macrophages," *Am. J. Respir. Cell Mol. Biol.* 12:190–195 (1995).

W. Hsueh et al., "$LTB_4$ Production and Lysosomal Enzyme Release by Rat Alveolar Macrophages: Effects of Phagocytosis, Receptor Binding, and Ionophore Stimulation," *Exp. Lung Res.* 13:385–399 (1987).

G. Rosen et al., "Free Radicals and Phagocytic Cells, "*FASEB J.* 9:200–209 (1995).

N. Hubbard and K. Erickson, Role of 5'–Lipoxygenase Metabolites in the Activation of Peritoneal Macrophages for Tumoricidal Function, *Mol. Immunol.* 160:115–122 (1995).

N. Ahmed et al., "Transgenic Mice Expressing Rabbit C–Reactive Protein Exhibit Diminished Chemotatic Factor–Induced Alveolitis," *Am. J. Respir. Crit. Care Med.* 153:1141–1147 (1996).

W. Smith et al., "Characterization of 5–Lipoxygenase Inhibitors In Biochemical and Functional In Vivo Assays," *J. Pharmacol. Exp. Ther.* 275:1322–1338 (1995).

J. Drazen et al., Comparative Airway and Vascular Activities of Leukotrienes C–1 and In Vivo and In Vitro, *Proc. Natl. Acad. Sci USA* 77:4354–4358 (1980).

R. Harris et al., "Clinical Activity of Leukotriene Inhibitors," *Int. J. Immunopharmac.* 17(2):147–156 (1995.

R. Malaviya et al., "Reversible Translocation of 5–Lipoxygenase in Mast Cells Upon IgE," *JBC* 268(7):4939–4944 (1993).

I. Pavord et al., "Effect of Inhaled Prostaglandin $E_2$ on Allergen–Induced Asthma," *Am Rev Respir. Dis*148:87–90 (1993).

M. Baile et al., "Leukotriene–Deficient Mice Manifest Enhanced Lethality from Klebsiella Pneumonia in Association with Decreased Alveolar Macrophage Phagocytic and Bactericidal Activities," *The Journal of Immunology* 157:5221–5224 (1996).

ADMINISTRATION OF PRODUCTS OF THE 5-LIPOXYGENASE METABOLIC PATHWAY TO ENHANCE ANTIMICROBIAL DEFENSE

FIELD OF THE INVENTION

The present invention relates generally to the administration of compounds to enhance antimicrobial defense, and more particularly to the administration of products of the 5-lipoxygenase metabolic pathway to enhance bacterial defense and to treat and prevent bacterial pneumonia.

This invention was made with United States government support awarded by the National Institute of Health (NIH), Grant Nos. HL 58200, HL 57243, AA 10571, P 50 HL 46487, CA 66180, HL 50057, and HL 47391.

BACKGROUND OF THE INVENTION

A. Pulmonary Host Defense and the Pathogenesis of Pneumonia

In view of the constant challenge to the respiratory tract from inhaled or aspirated microbes, and the deleterious consequences of unchecked infection, an efficient system of pulmonary antimicrobial defense is obviously important to health. Microbes which elude the mechanical defenses offered by the upper respiratory tract and airways reach the alveoli. Here, the alveolar macrophage normally serves as the defender of mucosal sterility, patrolling the alveolar surface and clearing organisms by phagocytosis and intracellular killing. [M. Lohmann-Matthes et al., Eur. Respir. J. 7:1678–1689 (1994)]. If the microbial load exceeds the local clearance capacity of the resident alveolar macrophages, the macrophages can elaborate chemotactic factors which recruit circulating neutrophils to the airspaces and activate their phagocytic and microbicidal activities.

Although phagocytic cells are capable by themselves of microbial ingestion, the efficiency of this process is enhanced by the presence of various soluble molecules (opsonins) which coat the organisms and mediate their attachment to surface receptors on the phagocyte. These opsonins include immunoglobin as well as factors which coat microbes nonspecifically, such as the complement fragment C3b, surfactant protein A, and fibronectin. Likewise, phagocytosis and intracellular killing are further augmented by a variety of activating agents, including colony stimulating factors, chemokines, and lipids. Unfortunately, qualitative or quantitative impairment of any component of these defenses can compromise bacterial clearance and predispose to pneumonia. [See, e.g., J Langermans et al., J. Immunol. Methods 174:185–194 (1994)].

B. Significance of Bacterial Pneumonia

In industrialized nations, pneumonia is associated with greater morbidity and mortality than any other type of infection. Overall, it is the sixth leading cause of death in the United States. In adults greater than 65 years of age, it is the fourth most common reason for hospitalization. Among hospital-acquired infections, pneumonia is the second most common in incidence and the most commonly fatal.

Bacteria are the etiologic pathogens in a substantial proportion of community-acquired pneumonias and in the great majority of nosocomial pneumonias. Frequently, enteric Gram-negative organisms are the etiologic microbes responsible for both types of pneumonia. Gram-negative pneumonias are generally thought to result from microaspiration of oral secretions, and are therefore particularly likely in individuals demonstrating oropharyngeal colonization with these organisms. This is especially common in hospitalized patients, particularly those in intensive care units, but also occurs in alcoholics, patients with underlying systemic illness or impairments in host defense, and those with chronic pulmonary disease. [S. Nelson et al., Clin. Chest Med. 16:1–12 (1995)].

C. Antibiotic Therapy

Due to the widespread use and frequent over-prescribing of antimicrobial agents, there is an increasing incidence of microbes acquiring drug-resistance. In other words, organisms typically susceptible (i.e., inhibited or killed) to a particular antimicrobial agent are no longer susceptible. This is especially important with regard to the use of antibiotics in the treatment of bacterial infections.

Acquired drug resistance is usually caused by a mutation within the genome of the microbe or by the acquisition of a plasmid. For example, one of the major mechanisms of resistance to the β-lactam antibiotics, including penicillins, is the production of β-lactamases. Moreover, resistance to one member of a class of agents (e.g., the aminopenicillin ampicillin) can result in complete cross-resistance to other members of that class (e.g., the aminopenicillin amoxicillin).

Antibiotic pressure in certain patient populations (e.g., patients with underlying systemic illness or impairments in host defense) has contributed to the development of infections with multi-drug resistant organisms, the eradication of which is increasingly difficult. One factor contributing to antibiotic pressure is the widespread use of antibiotics in the hospital setting, especially in the critical care units. Indeed, physicians are frequently forced to utilize antibiotic regimens comprising multiple agents to combat such infections or to use broad-spectrum agents (e.g., Primaxin®, Merck) generally reserved for the most serious infections.

What is needed is a means for enhancing pulmonary defense capabilities that either requires no antibiotics or can be used to augment antibiotic treatment. The enhancement means should be efficacious in the treatment and prevention of bacterial pneumonia in those patients who are especially susceptible thereto, should have a rapid onset of action, and should not elicit immunological reactions in the recipient.

SUMMARY OF THE INVENTION

Leukotrienes are potent mediators of inflammation derived from the 5-lipoxygenase pathway of arachidonic acid metabolism. These substances have been implicated in the pathogenesis of inflammatory lung diseases, and new pharmacologic agents that inhibit leukotriene synthesis or actions have recently become available for the treatment of asthma. The present invention contemplates the use of leukotrienes and other products of the 5-lipoxygenase pathway as an adjunct in the treatment of pneumonia and other lower respiratory tract infections.

In order to evaluate the role of leukotrienes in bacterial pneumonia, the present inventors have employed a model of Klebsiella pneumonia in knockout mice rendered leukotriene-deficient by the targeted disruption of the 5-lipoxygenase gene. The present inventors found that leukotriene production was increased in the lungs of infected wild type mice, and that leukotriene-deficient animals manifested reduced bacterial clearance and enhanced lethality. Moreover, alveolar macrophages from knockout mice exhibited impaired in vitro phagocytosis and killing of *K. pneumoniae*, and this functional defect in leukotriene-deficient alveolar macrophages was overcome by the addition of exogenous leukotrienes such as $LTB_4$. Importantly, intrapulmonary administration of $LTB_4$ partially overcame the in vivo impairment in bacterial clearance observed in knockout mice.

The present inventors have determined that endogenous leukotrienes play an integral role in the host response to pulmonary infection. Even more importantly from a therapeutic standpoint, the present inventors found that exogenous leukotrienes exert pharmacologic actions which augment this response.

The present invention contemplates the treatment of patients with a recognized predisposing factor (e.g., smoking, alcoholism, diabetes, HIV infection, known aspiration) for overwhelming pneumonia, or with early pneumonia, with administration via inhalation or an endotracheal tube of metabolic products of the 5-lipoxygenase pathway (e.g., leukotrienes). In addition, the present invention contemplates the use of the products of the 5-lipoxygenase pathway for prophylactic purposes. While an understanding of the mechanism by which the products act is not necessary for the successful practice of the present invention, the administration of such products, especially the intrapulmonary administration of leukotrienes, augments local endogenous host defense mechanisms and assists in bacterial infection eradication during antibiotic administration. The products have a relatively short duration of action (e.g., hours), do not cause antibody-mediated immune responses, and are relatively inexpensive.

The present invention is not limited to the intrapulmonary administration of products of the 5-lipoxygenase pathway for the treatment of pneumonia. Indeed, the present invention contemplates the administration of these products via other routes of administration and for the treatment and prevention of other conditions. The products may be administered concomitantly with antibiotics in some embodiments. In other embodiments, different products (e.g., $LTB_4$ and $LTC_4$) of the 5-lipoxygenase pathway are administered together or at defined intervals, with or without the concomitant administration of antibiotics.

The present invention contemplates a method of enhancing antimicrobial defense, comprising administering an effective amount of a therapeutic composition to a host suspected of having a microbial infection, the composition comprising a product of the 5-lipoxygenase pathway. In addition, the present invention contemplates a method of enhancing antimicrobial defense, comprising administering an effective amount of a therapeutic composition to a host for prophylactic purposes, the composition comprising a product of the 5-lipoxygenase pathway. Such prophylactic administration is most frequently performed with patients who are at high risk for developing a microbial infection. Patients who are at high risk include, but are not limited to, patients with the AIDS virus and other patients who are immunocompromised.

In one embodiment, the microbial infection is bacterial pneumonia. In particular embodiments, the product of the 5-lipoxygenase pathway comprises a leukotriene. When the product of the 5-lipoxygenase pathway comprises a leukotriene, the leukotriene is leukotriene $B_4$ in certain embodiments and a cysteinyl leukotriene (e.g., leukotriene $C_4$, leukotriene $D_4$, and leukotriene $E_4$) in other embodiments. In still further embodiments, the method of administering comprises pulmonary administration, and the pulmonary administration is by aerosolization of the therapeutic composition in other embodiments. Moreover, certain embodiments further involve the co-administration of an antibiotic to the host. The host is an animal in some embodiments, and a human in others.

Furthermore, the present invention contemplates a method of treating a bacterial infection, comprising administering an effective amount of a therapeutic composition to a host having a bacterial infection, the therapeutic composition comprising a leukotriene. In particular embodiments, the bacterial infection is bacterial pneumonia. The leukotriene is leukotriene $B_4$ in certain embodiments and a cysteinyl leukotriene like leukotriene $C_4$, leukotriene $D_4$, and leukotriene $E_4$ in other embodiments. In still further embodiments, the method of administering comprises pulmonary administration, and the pulmonary administration is by aerosolization of the therapeutic composition in other embodiments. Moreover, certain embodiments further involve the co-administration of an antibiotic to the host. The host is an animal in some embodiments, and a human in others.

Finally, the present invention contemplates a solution for the treatment of a microbial infection, the solution comprising a sterile liquid vehicle and a leukotriene dissolved in the sterile liquid vehicle. In particular embodiments, the leukotriene is leukotriene $B_4$. In still further embodiments, the leukotriene is a cysteinyl leukotriene; when the leukotriene is a cysteinyl leukotriene, it is leukotriene $C_4$, leukotriene $D_4$, or leukotriene $E_4$ in particular embodiments. Finally, the solution is aerosolized in still additional embodiments.

DEFINITIONS

To facilitate understanding of the invention set forth in the disclosure that follows, a number of terms are defined below.

The phrase "product of the 5-lipoxygenase pathway" refers to those compounds that result from the enzymatic conversion of arachidonic acid by 5-lipoxygenase. Products of the 5-lipoxygenase pathway include 5-hydroperoxyeicosatetraenoic acid [5-HPETE] and $LTA_4$, as well as compounds derived therefrom. The products encompass 5-HETE, which is produced from 5-HPETE. The products also include compounds formed from the conversion of $LTA_4$, such as $LTB_4$, $LTC_4$, $LTE_4$, and $LTF_4$. Moreover, the products are meant to encompass derivatives (i.e., compounds produced by structural modification) of compounds produced in the arachidonic acid cascade. The present invention is not limited by the nature of the structural modification; modifications include, but are not limited to, the formation of a double bond between two carbon atoms and the addition of functional groups like hydroxyl and carboxy moieties. Further modifications contemplated by the present invention include the substitution of different amino acids for those normally present (e.g., the replacement of the glycine residue on $LTD_4$ with another amino acid) or the attachment of additional amino acids. The following table (Table 1) lists various commercially available products (Cayman) of the 5-lipoxygenase pathway. Of course, the present invention is not limited to those compounds set forth in Table 1.

TABLE 1

| Parent Compound | Derivative Compounds |
|---|---|
| Leukotriene $A_4$ | Leukotriene $A_4$ methyl ester |
| Leukotriene $B_3$ | |
| Leukotriene $B_4$ | Leukotriene $B_4$-$d_4$ |
| | Leukotriene $B_4$ dimethyl amide |
| | 6-trans Leukotriene $B_4$ |
| | 6-trans-12-epi Leukotriene $B_4$ |
| | 12-epi Leukotriene $B_4$ |
| | 18-carboxy dinor Leukotriene $B_4$ |
| | 20-carboxy Leukotriene $B_4$ |
| | 20-hydroxy Leukotriene $B_4$ |
| Leukotriene $B_5$ | |
| Leukotriene $C_4$ | |
| Leukotriene $C_5$ | |

TABLE 1-continued

| Parent Compound | Derivative Compounds |
| --- | --- |
| Leukotriene $D_4$ | |
| Leukotriene $D_5$ | |
| Leukotriene $E_4$ | N-acetyl Leukotriene $E_4$ |
| | 16-carboxy-$\Delta^{13}$-tetranor Leukotriene $E_4$ |
| | N-acetyl-16-carboxy-$\Delta^{13}$-tetranor $LTE_4$ |
| | fluoro Leukotriene $E_4$ |
| Leukotriene $E_5$ | |
| Leukotriene $F_4$ | |
| Leukotriene Mixtures | Peptido-Leukotriene Mixtures |
| | Leukotriene $A_4$ Metabolite Mixture |
| | Leukotriene $E_4$ Metabolite Mixture |

The term "leukotriene" is herein defined functionally as those compounds causing enhancement of antimicrobial defense. The term "microbial" includes, but is not limited to, bacteria, viruses, parasites, and fungi.

The term "cysteinyl leukotriene" refers to those leukotrienes that possess the cysteine residue characteristic of leukotrienes $C_4$, $D_4$, and $E_4$.

The term "eicosanoid" refers to compounds derived from 20-carbon essential fatty acids that contain three, four, or five double bonds: 8,11,14-eicosatrienoic acid (dihomo-$\gamma$-linolenic acid), 5,8,11,14-eicosatetraenoic acid (arachidonic acid), and 5,8,11,14,17-eicosapentaenoic acid. The families of leukotrienes and prostaglandins are examples of eicosanoids.

The term "effective amount" refers to that amount of a 5-lipoxygenase product that is required to successfully perform a particular function. Generally speaking, the effective amount of a 5-lipoxygenase product will be that amount that enhances or improves (to any degree) the ability of the body to eradicate a microbial infection, especially a bacterial infection. The effective amount may depend on a number of factors, including the type of microbe involved, the severity of the infection, the immune status of the individual, and the weight of the individual. By way of example, leukotriene $LTD_4$ may be administered in a therapeutic composition containing between 0.1 $\mu$g and 10 $\mu$g.

The term "therapeutic composition" refers to a composition that comprises a product of the 5-lipoxygenase pathway (e.g., $LTB_4$ and $LTC_4$) in a pharmaceutically acceptable form. The characteristics of the form will depend on a number of factors, including the mode of administration. For example, a composition for aerosolized pulmonary administration must be formulated such that the product is pharmacologically active following delivery to the lungs. The therapeutic composition may contain diluents, adjuvants and excipients, among other things. In a preferred embodiment, the product of the 5-lipoxygenase pathway is dissolved in a sterile liquid vehicle. The term "sterile liquid vehicle" refers to those liquids that are suitable for administration to a host (e.g., pulmonary or parenteral administration) and allow dissolution of the product of the 5-lipoxygenase pathway. Examples of sterile liquid vehicles include, but are not limited to, sterile normal saline and dilute concentrations of ethanol.

The term "host" refers to humans and animals.

The terms "enhancing microbial defense" and "enhancing bacterial defense" refer broadly to the improved ability of a subject's immune system to respond to and eradicate a microbial infection (e.g., a bacterial, parasitic, viral, and fungal infection) and specifically a bacterial infection, respectively. The terms include, for example, augmentation of the subject's endogenous defense mechanisms. The presence of enhancement of antimicrobial/antibacterial defense is determined by subjecting a compound to the screening procedure described in Table 3 below.

DESCRIPTION OF THE INVENTION

The present invention relates generally to the administration of compounds to enhance microbial defense, and more particularly to the administration of products of the 5-lipoxygenase metabolic pathway to enhance bacterial defense and to treat and prevent bacterial pneumonia. To facilitate an understanding of the present invention, the description that follows is divided into the following sections: I) Synthesis, Actions, and Pharmacologic Modulation of Leukotrienes; II) Leukotrienes and Antimicrobial Host Defense; III) 5-LO Activation in Alveolar Macrophages and Neutrophils; IV) Role of Leukotrienes in the In Vivo Host Response; and V) Composition and Administration of Compounds.

I. Synthesis, Actions, and Pharmacologic Modulation of Leukotrienes

Figure 1A:
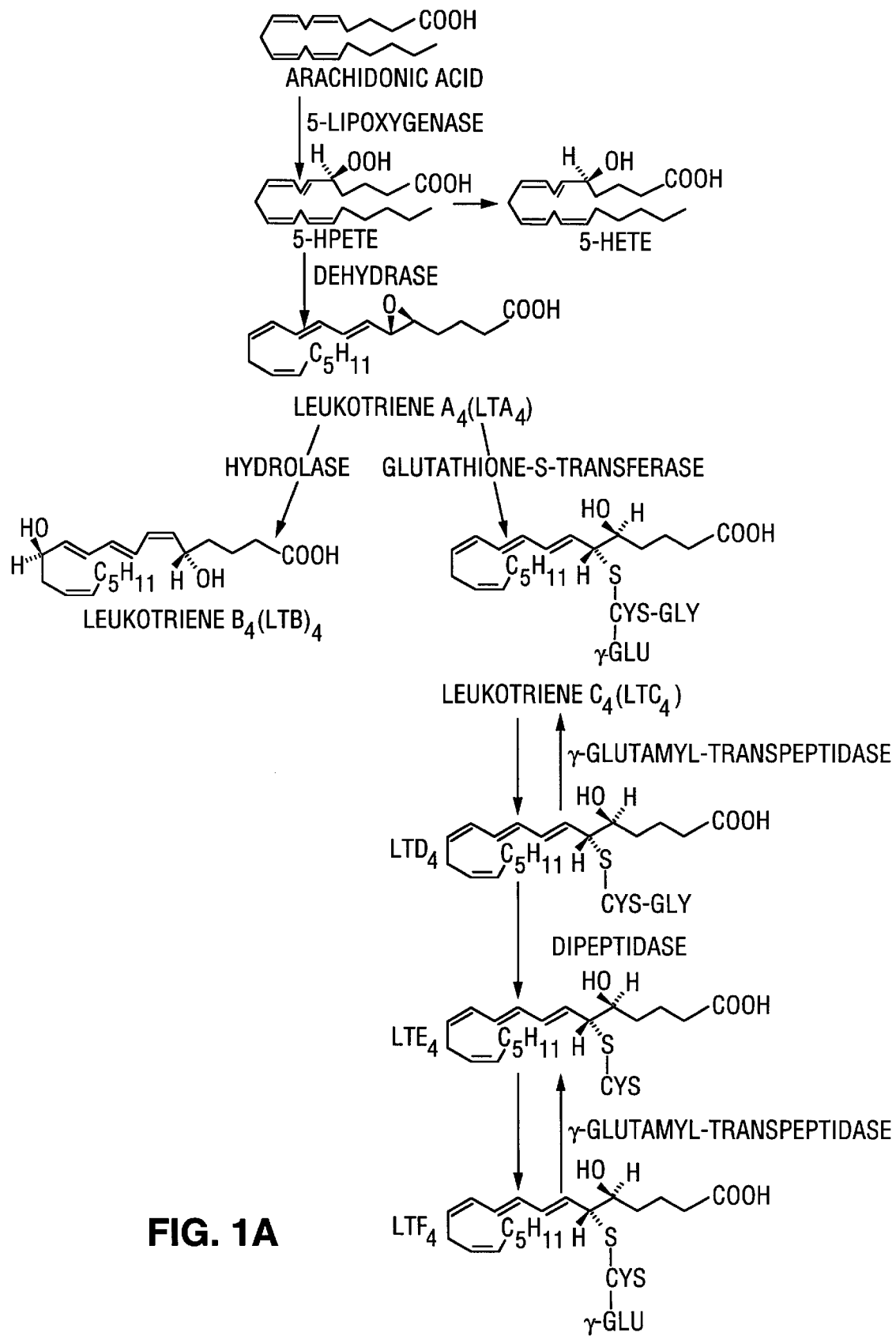
FIG. 1A is a schematic depicting the pathway of leukotriene synthesis and the structures of the main products of the 5-lipoxygenase metabolic pathway.

Leukotrienes are oxygenated derivatives of arachidonic acid synthesized mainly by bone marrow-derived cells in response to a variety of soluble or particulate stimuli. [E. Goetzl et al., FASEB J 9:1051–1058 (1995)]. Arachidonic acid is initially hydrolyzed from membrane phospholipids, in part by the actions of cytosolic phospholipase $A_2$ ($cPLA_2$). The next two steps in leukotriene synthesis (the sequential conversion of arachidonic acid first to 5-hydroperoxyeicosatetraenoic acid [5-HPETE] and then to $LTA_4$) are catalyzed by the enzyme 5-lipoxygenase (5-LO). This enzyme resides within the cytosol and/or the nucleus of resting cells. Though an understanding of its mechanism of action is not required in order to practice the present invention, upon agonist stimulation, it is believed that 5-LO translocates in a $Ca^{2+}$-dependent manner to the nuclear envelope [see, e.g, J. Woods et al., J. Clin. Invest. 95:2035–2040 (1995)]; here it is thought to gain access to free arachidonic acid, hydrolyzed from nuclear envelope phospholipids and presented by the integral nuclear envelope arachidonic acid-binding protein, 5-LO activating protein (FLAP). 5-HPETE can be converted to the stable product, 5-HETE. The $LTA_4$ can be enzymatically converted to $LTB_4$ (by $LTA_4$ hydrolase) or to $LTC_4$ (by $LTC_4$ synthase). In turn, $LTC_4$ can be enzymatically converted to $LTD_4$ (with concomitant increase in bioactivity) and then to $LTE_4$; $LTE_4$ may be subsequently modified to form $LTF_4$. FIG. 1A is a schematic depicting the pathway of leukotriene synthesis and the structures of the main products of the 5-lipoxygenase metabolic pathway; importantly, practice of the present invention does not depend on the accuracy of the model depicted in FIG. 1A.

Cellular leukotriene synthetic capacity can be enhanced by exposure to a number of biologically active substances, such as granulocyte-macrophage colony-stimulating factor, interferon-γ, and transforming growth factor-β. As described in further detail below, alveolar macrophages have a greater capacity for 5-LO metabolism than do blood monocytes or other tissue macrophages [see, e.g., M. Peters-Golden et al., J. Immunol. 144:263–270 (1990)], and they produce both $LTB_4$ and $LTC_4$. Neutrophils, by contrast, produce only $LTB_4$. Alveolar macrophages and neutrophils both produce 5-HETE.

Though an understanding of their mechanism of action is not required in order to practice the present invention, the principle bioactive leukotrienes, $LTB_4$ and the cysteinyl or sulfidopeptide leukotrienes (leukotrienes $C_4$, $D_4$, and $E_4$), are thought to act by interacting with specific surface receptors on target cells. $LTB_4$ is a potent neutrophil chemotaxin in vitro, accounting for the majority of chemotactic activity elaborated acutely by stimulated human alveolar macrophages in culture. [T. Martin et al., J. Clin. Invest. 80:11 14–1124 (1989)]. In addition, in vivo bronchoscopic instillation of $LTB_4$ into the human lung resulted in neutrophil influx. [T. Martin et al., J. Clin. Invest. 80:1009–1019 (1989)].

While the practice of the present invention does not depend on a precise understanding of the effects of the products of the 5-LO pathway, $LTB_4$ is thought to enhance numerous leukocyte functions, including phagocytosis [T. Demitsu et al., Int. J. Immunopharmac. 11:801–808 (1989)], upregulation of cell surface CR3 molecules [P. Marder et al., Biochem. Pharmacol. 49:1683–1690 (1995)], the secretion of $O_2^-$ and lysosomal hydrolases, mobilization of intracellular $Ca^{2+}$ stores [C. Serhan et al., Biochem. Biophys. Res. Commun. 107:1006–1012 (1982)], phospholipase-dependent arachidonic acid release [J. Wijkander et al., J. Biol. Chem. 270:26543–26549 (1995)], activation of PKC [J. O'Flaherty et al., J. Immunol. 144:1909–1913 (1990)], the synthesis of interleukin (IL)-8 [R. Strieter et al., Am. J. Pathol. 141:397–407 (1992)], and activation of natural killer cell activity [R. Bray and Z. Brahmi Z, J. Immunol. 136:1783–1790 (1986)]. It is believed that 5-HETE shares many of these same actions, but with less potency. The cysteinyl leukotrienes possess the bioactivity previously identified as slow reacting substance. Their most potent actions include constriction of bronchial and vascular smooth muscle and increasing microvascular permeability. $LTD_4$ has also been reported to increase macrophage FcR expression in vitro [J. Rhodes et al., Eur. J. Immunol. 15:222–227 (1985)] and actin polymerization [M. Peppelenbosch et al., Cell 74:565–575 (1993)].

Though an understanding of the molecular mechanisms of bacterial ingestion and killing by phagocytes is not required in order to practice the present invention, the phagocyte surface receptors which are most critical for efficient opsonic phagocytosis are those which recognize the Fc portion of IgG (FcRII and FcRIII) and the C3bi fragment of complement (the integrin CR3, also known as Mac-1 and CD11b/CD18). CR3 also mediates nonopsonic ingestion of K. pneumoniae. One consequence of receptor ligation is the release and metabolism of arachidonic acid. Because CR3 and FcR mediate attachment of K. pneumoniae to phagocytes, their surface expression are relevant targets for modulation by leukotrienes.

Figure 1B:
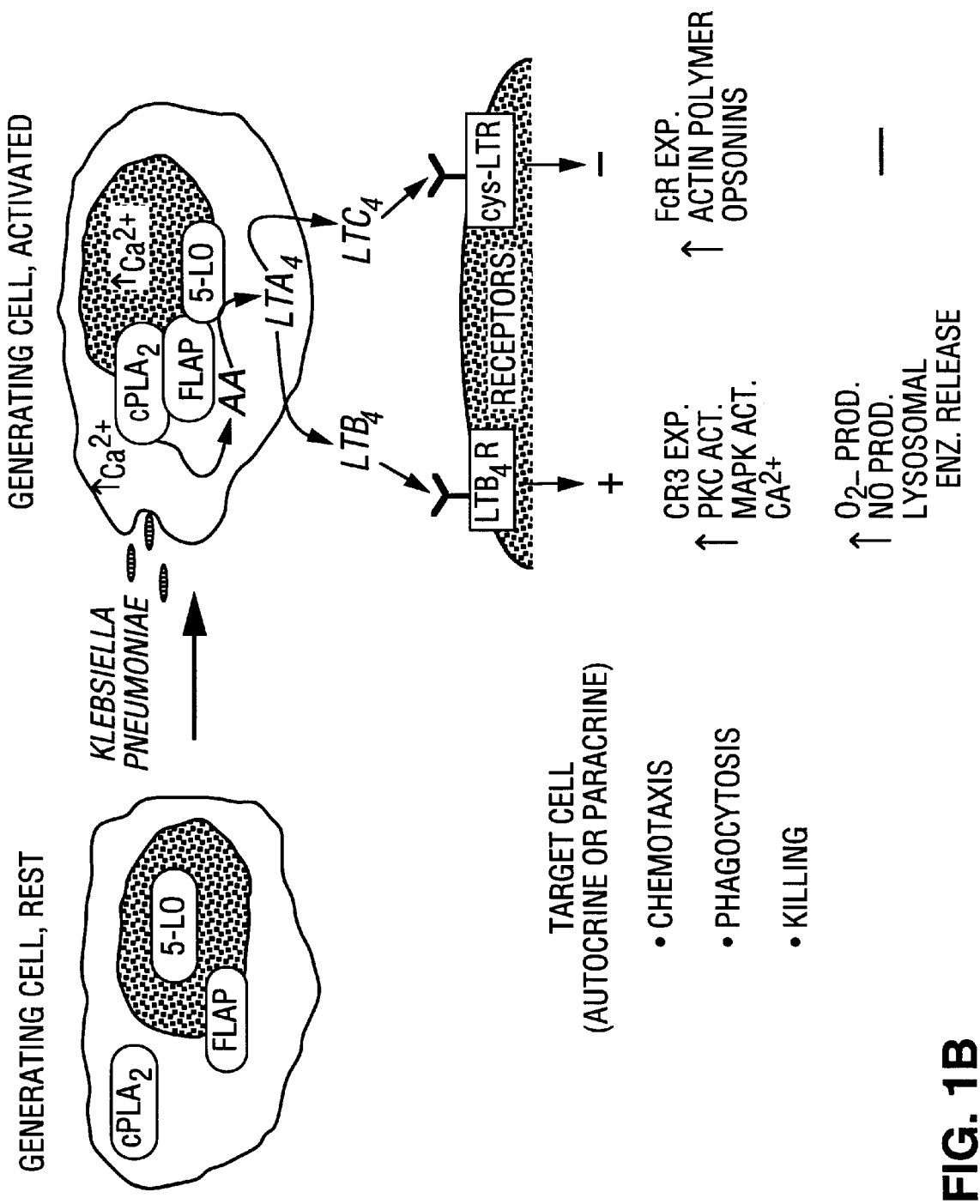
FIG. 1B is a schematic overview depicting the pathway of leukotriene synthesis and the actions of leukotrienes relevant to antimicrobial defense.

FIG. 1B is a schematic depicting the pathway of leukotriene synthesis and the actions of leukotrienes relevant to antimicrobial defense. Bacteria, such as K pneumoniae, attach to phagocytic cells such as alveolar macrophages and neutrophils and are phagocytosed. It is believed that this triggers an increase in intracellular $Ca^{2+}$, which in turn results in translocation of $cPLA_2$ and 5-LO to the nuclear envelope. As previously indicated, arachidonic acid is hydrolyzed from phospholipids and metabolized by 5-LO, interacting with FLAP, to $LTA_4$. $LTA_4$ is further converted to leukotrienes $B_4$ and $C_4$. These may affect target cells, via interactions with receptors, in either autocrine or paracrine fashion. As a result, chemotaxis, bacterial phagocytosis, and bacterial killing are promoted.

Interruption of the synthesis or actions of leukotrienes has been a prime therapeutic target of the pharmaceutical industry. Potent and specific compounds are now available which inhibit leukotriene synthesis by directly inhibiting either 5-LO or FLAP; both classes of agents inhibit synthesis of all 5-LO products. In addition, compounds which specifically antagonize the $LTB_4$ and cysteinyl leukotriene receptors are also available; unlike the former class, these agents offer the capability to block the actions of individual leukotrienes independently. Although preclinical studies suggest a variety of potential disease targets, asthma has received the most attention in clinical studies.

II. Leukotrienes and Antimicrobial Host Defense

It is generally assumed that inflammatory cascades have evolved for the purpose of host defense against microbial invasion. Yet little is known about the possible importance of endogenous leukotrienes in mediating the host response to infection. The increasing incidence of immunosuppression and the emergence of antibiotic-resistant microbes underscore the importance of understanding the innate host defense mechanisms.

The sterility of the pulmonary alveolar surface is under constant assault by inhaled and aspirated microbes. Effective clearance of these pathogens depends largely on innate immune responses involving microbial phagocytosis and killing. Prior to the work of the present inventors, researchers have largely ignored the products of the 5-LO pathway as potentially representing a class of inflammatory mediators in antimicrobial defense.

The present inventors have found that exogenously administered products of the 5-LO pathway in general, and leukotrienes in particular, are associated with a number of possible advantages as adjunctive agents in the treatment of pneumonia. Specifically, the inventors have determined that these products exhibit a rapid onset of action and believe that these products do not elicit immunologic responses in the recipient. Moreover, such products represent a relatively inexpensive therapy that can be used independent of antibiotics or as adjunct therapy to antibiotics in the treatment of pneumonia. Particular patient populations (e.g., patients with AIDS, diabetes, smokers, neonates, and patients suffering from alcoholism and malnutrition) with severe pneumonia would benefit from augmenting endogenous host defense mechanisms through the rational administration of, for example, leukotrienes to the lungs.

Though a precise understanding of the effects of leukotrienes on antimicrobial host defense is not required to practice the present invention, it is believed that certain general effects occur. First, endogenous leukotrienes must be present at sites of infection in order to participate in antimicrobial defense, and increased (relative to controls) levels of $LTB_4$ have been measured in bronchoalveolar lavage fluid (BALF) and lung tissue of *Pseudomonas aeruginosa*-infected rats [A. Buret et al., Infect. Immun. 61:671–679 (1993)] as well as bronchoalveolar lavage fluid of patients with bacterial pneumonia [H. Hopkins et al., Chest 95:1021–1027 (1989)]. As described in further detail below, the present inventors have also measured high levels of both $LTB_4$ and $LTC_4$ in lung homogenates of mice with Klebsiella pneumonia. *Klebsiella pneumoniae* is the classic cause of Gram-negative pneumonia and has been reported to account for 18–64% of community-acquired and 30% of nosocomial Gram-negative pneumonias. [L. Crane and A. Lerner, In: *Respiratory Infections: Diagnosis and Management* (J. Pennington, ed.) (Raven Press, New York), pp. 227–250 (1983)].

Second, exogenously added leukotrienes enhance microbial phagocytosis and/or killing. As described above, the addition of $LTB_4$ promotes neutrophil chemotaxis as well as phagocytosis of particles, signal transduction, and secretion of oxidants and lysosomal enzymes—all of which would be expected to facilitate bacterial clearance. Indeed, $LTB_4$ enhanced the in vitro phagocytosis and killing of *P. aeruginosa* and *Salmonella typhimurium* by peritoneal macrophages [T. Demitsu et al., Int. J. Immunopharmac. 11:801–808 (1989)], and the in vitro killing of *Schistosoma mansoni* by neutrophils [R. Moqbel et al., Clin. Exp. Immunol. 52:519–527 (1983)]; intraperitoneal injection of $LTB_4$ also enhanced the in vivo clearance of S. typhimurium administered by the same route [T. Demitsu et al., Int. J. Immunopharmac. 11:801–808 (1989)]. However, prior to the present invention, it is believed that the intrapulmonary administration of leukotrienes and other products of the 5-LO pathway has not previously been reported for therapeutic use.

Third, reduction of endogenous leukotriene synthesis increases susceptibility to infection. Phagocytosis, degranulation, and nitric oxide production have been reported to be inhibited by relatively specific inhibitors of 5-LO, indicating a permissive role for endogenous leukotrienes in these functions. Interestingly, a number of situations characterized by predisposition to pulmonary infections are associated with a reduced in vitro capacity of alveolar macrophages to synthesize leukotrienes; these include both human conditions (HIV infection and smoking) as well as animal models (proteincalorie malnutrition, vitamin D deficiency, and the neonatal period). A similar association has been noted for peripheral blood leukocytes from patients with diabetes mellitus. This raises the possibility that a defect in 5-LO metabolism could underlie the multiple defects in leukocyte function which have been demonstrated in poorly controlled diabetics. Clinical use of anti-leukotriene agents in asthma has not been associated with an increase in respiratory infections. However, these studies have generally been short-term (i e., several weeks or months), and young otherwise healthy asthmatics are not a patient population which would be expected to be predisposed to such infections.

III. 5-LO Activation in Alveolar Macrophages and Neutrophils

Alveolar macrophages have been demonstrated to have a greater capacity for leukotriene synthesis than peripheral blood monocytes or other tissue macrophages. This is the situation in response to both soluble (ionophore A23187) and particulate (zymosan) agonists, and for cells from humans [M. Balter et al., J. Immunol. 142:602–608 (1989)] as well as rats [M. Peters-Golden et al., J. Immunol. 144:263–270 (1990)] (data not shown). Moreover, as described further in the Experimental section, the profile of eicosanoids released by stimulated murine alveolar macrophages is likewise comprised largely of 5-LO metabolites (see FIG. 2A).

The present inventors have also demonstrated that neutrophils recruited to sites of inflammation exhibit increased leukotriene synthetic capacity and a shift in intracellular 5-LO distribution. Indeed, the present inventors have compared leukotriene synthetic capacity and intracellular distribution of 5-LO in rat neutrophils isolated from peripheral blood or from peritoneal lavage fluid 4 hours after glycogen instillation. Elicited neutrophils exhibited a 5-fold greater maximal capacity for $LTB_4$ synthesis in response to A23187 than did blood neutrophils studied in parallel (data not shown). In addition, the two cell populations exhibited strikingly different intracellular distributions of 5-LO in the resting state. As previously demonstrated for human blood neutrophils [T.G. Brock et al., J. Biol. Chem. 269:22059–22066 (1994)], the resting rat blood neutrophils contained 5-LO exclusively in the cytosol. By contrast, the resting elicited neutrophils contained a substantial proportion of their 5-LO within the nucleus; upon subsequent ionophore activation, both blood and elicited neutrophil populations showed 5-LO translocation to the nuclear envelope (data now shown).

In addition to the findings, described above, with neutrophils recruited to the peritoneum, the present inventors have also observed a predominant intranuclear localization of 5-LO in neutrophils recruited to the alveolar space, as evidenced in rats studied 2 days post-intratracheal administration of bleomycin. This can be demonstrated both by immunofluorescence microscopic analysis of lavage cells and by immunohistochemical staining of lung sections (data not shown). In total, these results suggest that, in the process of recruitment from the bloodstream to diverse anatomic sites of inflammation, neutrophils i) import cytosolic 5-LO into the cell nucleus and ii) upregulate their maximal capacity for leukotriene generation. In both of these respects, recruited neutrophils resemble alveolar macrophages.

Importantly, it is known that there is reduced leukotriene synthetic capacity in alveolar macrophages from humans or animals predisposed to pulmonary infections. The present inventors have examined the 5-LO metabolic capacity of alveolar macrophages isolated from various human or animal conditions known to be associated with increased susceptibility to pulmonary infections. These conditions included controlled studies with human subjects who smoke [M. Balter et al., J. Lab. Clin. Med. 114:662–673 (1989)], human subjects infected with the human immunodeficiency virus (CD4 count less than 200) [M. Coffey et al., J. Immunol. 157:393–399 (1996)], vitamin D-deficient rats [M. J. Coffey et al., Prostaglandins 48:313–329 (1994)], newborn calves, and alcohol-fed mice. In all cases, the subjects had no evidence of bacterial lung infections at the time of study. In each of these circumstances, the in vitro capacity of alveolar macrophages for leukotriene synthesis was reduced by 60–90% as compared to the control levels. These findings indicate that the administration of exogenous leukotrienes should enhance the host defense mechanism in patients susceptible to lower respiratory tract infections.

IV. Role of Leukotrienes in the In Vivo Host Response

The development of leukotriene-deficient mice by targeted disruption of the 5-LO gene represents an important tool to evaluate the role of endogenously generated leukotrienes. [J. Goulet et al., Proc. Natl. Acad. Sci. USA 91:12852–12856 (1994); X. Chen et al., Nature 372:179–182 (1994)]. These knockout mice have been found to have a reduced ability to recruit neutrophils in most models of inflammation. The present inventors tested commercially available 5-LO knockout mice to further show that impaired endogenous leukotriene synthetic capacity is causally related to impaired antimicrobial defense of the lung.

The present inventors used *Klebsiella pneumoniae* as a causative pathogen to induce pneumonia for several reasons. First, as previously discussed, it is of great clinical relevance in pneumonia. Second, it causes a brisk inflammatory response in mice. [A. McColm et al., J. Antimicrob. Chemother. 18:599–608 (1986)]. Third, the murine *K. pneumoniae* model has been extensively characterized by one of the co-inventors. In the experiments described below, intratracheal (i.t.) injection was utilized rather than aerosolization because it more closely resembles the bolus of organisms which reaches the distal lung via microaspiration. Following intratracheal challenge of CD-1 mice with $10^3$ CFU of *K. pneumonia*, neutrophil influx peaks at 48 hours and most animals have died by day 5. In addition, lung homogenate levels of various cytokines increase and also peak at 48 hours; these include tumor necrosis factor (TNF), macrophage inflammatory protein-2 (MIP-2), macrophage inflammatory protein-1α (MIP-1α), IL-12, and IL-10.

In order to apply this model of pneumonia to 5-LO knockout mice, the present inventors first identified an inoculum of organisms which was appropriate for the wild type background strain, 129/SvEv. This strain of mice proved to be even more susceptible to Klebsiella pneumonia than the CD-1 strain. Specifically, previous studies determined that approximately 50% mortality occurred in the wild type animals with a bacterial inoculum of only 50 CFU, indicating that 129/SvEv mice were substantially more susceptible to Klebsiella pneumonia than the CD-1 strain. [M. Greenberger et al., J. Immunol. 155:722 (1995)]. The requirement for a low bacterial inoculum makes this a relevant experimental model for Gram-negative pneumonia in humans, which is generally believed to result from microaspiration of oropharyngeal contents containing relatively small numbers of organisms.

Though the present invention utilizes a murine K. pneumonia model, the present invention is not limited to augmenting the treatment of infections caused by that organism. Indeed, the present invention contemplates the administration of products of the 5-LO metabolic pathway, particularly $LTB_4$ and $LTC_4$, independently and as an adjunct (e.g., with antibiotics) to the treatment of pneumonia and other respiratory tract infections caused by a panoply of organisms. Table 2 lists some of the most common bacterial pathogens that cause community-acquired and hospital-acquired pneumonia. It is contemplated that patients with infections caused by these organisms will benefit from administration of the products of the 5-LO metabolic pathway.

TABLE 2

| Type of Pneumonia | Type of Pathogen |
| --- | --- |
| Community Acquired | most frequent: |
| | *Streptococcus pneumoniae*<br>*Haemophilus influenzae*<br>*Mycoplasma pneumoniae*<br>less frequent: |
| | *Staphylococcus aureus*<br>Legionella sp.<br>Gram-negative bacilli (alcoholics)<br>aspiration: |
| | mouth anaerobes (e.g., Peptococci spp.) |
| Hospital Acquired | most frequent: |
| | Enterobacteriaceae (e.g., Klebsiella spp., *E. coli*)<br>*Pseudomonas aeruginosa*<br>*Staphylococcus aureus*<br>aspiration: |
| | mouth anaerobes |

The present invention is not limited to augmentation of the treatment of pneumonia. Indeed, the present invention contemplates the administration of products of the 5-LO metabolic pathway as therapy in the treatment of other infections that have pulmonary manifestations. Moreover, as alluded to above, the present invention contemplates the administration of the products for the treatment and prophylaxis of a broad range of microbial infections besides bacterial infections, including infections caused by parasites [R. Moqbel et al., Clin. Exp. Immunol. 52:519–527 (1983)], viruses, and fungi. Furthermore, the present invention contemplates augmentation of the treatment of systemic infections; it should be pointed out that systemic administration should be performed cautiously, as the leukotrienes are known to cause hypotension.

Moreover, while the present invention contemplates in vivo pulmonary administration of leukotrienes and other 5-LO products to augment defense against bacteria in leukotriene-deficient hosts, the present invention also contemplates in vivo administration to patients who are not leukotriene-deficient; indeed, such use is supported by the fact that in vitro incubation with exogenous leukotrienes augments phagocytosis and killing by normal macrophages.

Of note, the future use of anti-leukotriene drugs in humans is likely to mimic the leukotriene deficiency observed with 5-LO gene disruption in mice. In certain individuals who are on other immunosuppressive agents or who have increased numbers of bacteria in their lower respiratory tracts, the use of such drugs may compromise pulmonary antimicrobial host defense. As a result, these individuals may also benefit from administration of products of the 5-LO pathway contemplated for use with the present invention; of course, particular dosing schedules and regimens may be warranted when these agents are used concomitantly with patients taking anti-leukotriene drugs.

As previously alluded to, the present invention contemplates the use of diverse products of the 5-lipoxygenase metabolic pathway in order to enhance bacterial defense. The comprehensive screening procedure set forth in Table 3 can be used to evaluate those products (such as those compounds previously presented in Table 1), as well as derivatives or analogues of such products, that may be effective. Leukotrienes $B_4$ and $C_4$ are particularly effective at enhancing bacterial defense, and this screen is especially appropriate for compounds related to those leukotrienes. Reference to a particular example is given with each determination; the indicated examples provide a detailed description of how the determination is to be carried out.

TABLE 3

| Step | Determination | Conclusion |
| --- | --- | --- |
| I | Measure in vitro the activity of compounds on alveolar macrophage phagocytic and bactericidal activities (see, e.g., Example 3). | Proceed to Step II with those compounds that increase phagocytic and bactericidal activities. |
| II | Determine in vivo the effect of compounds on bacterial clearance after 48 hours by measuring CFU in lung homogenate (see, e.g., Example 2). | Proceed To Step III with those compounds that increase clearance. |
| III | Determine in vivo the effect of compounds via different routes of administration and administered at different time points post-bacterial challenge (see, e.g., Example 10). | Proceed to Step IV with those compounds that exhibit efficacy following the administration via at lease one route. |
| IV | Verify the findings of Step III by examining animal survival. | Consider clinical trials. |

As illustrated by this outline of the sequence of experimental procedures and the description of the procedures themselves, thoughtful consideration allows any compound (e.g., "Compound X") to be evaluated for use with the present invention. Indeed, as described in detail in the Experimental section, these screening procedures have been employed in the experiments performed with $LTB_4$.

V. Composition And Administration Of Compounds

The present invention contemplates using therapeutic compositions of products of the 5-LO metabolic pathway that are indicated as being efficacious based on application of the screen described above. It is not intended that the present invention be limited by the particular nature of the therapeutic preparation. For example, such compositions can be provided together with physiologically tolerable liquid (e.g, saline), gel or carriers or vehicles, diluents, adjuvants and excipients, such as pharmaceutical grades of mannitol, lactose, starch, magnesium stearate, sodium saccharin, cellulose, magnesium carbonate, and the like, and combinations thereof. These compositions typically contain 1%–95% of active ingredient, preferably 2%–70%. In addition, if desired the compositions may contain minor amounts of auxiliary substances such as wetting or emulsifying agents, stabilizing or pH buffering agents or preservatives. Generally speaking, the nature of the composition will depend on the method of administration.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts and the organism involved.

A preferred mode of administration comprises administration to the lung. Patients who are sick enough to require mechanical ventilation can receive treatment with pharmacologic agents administered via the endotracheal tube which is connected to the ventilator. Alternatively, intrapulmonary delivery of pharmacologic agents to patients not requiring mechanical ventilation can be accomplished via aerosolization. Alternatively, the agent may be administered to the lung through a bronchoscope. Of course, the therapeutic agents may be investigated for their efficacy via other routes of administration, including parenteral administration. However, when the site of infection is the lung, targeting drug delivery thereto is likely to minimize side effects and systemic consequences.

In addition, the compounds contemplated by the present invention possess attributes as therapeutic agents over other agents like polypeptides. For example, the products of the 5-LO metabolic pathway contemplated by the present invention have a rapid onset of action (generally within 1 hour) and short duration of action (generally less than 12 hours); these attributes permit a substantial degree of control over biological effects. In addition, their short duration of action reduces the possibility that administration of leukotrienes and related agents might adversely stimulate an over-exuberant inflammatory response. Moreover, commercially-available leukotriene receptor antagonists (e.g., the cysteinyl antagonist Accolate® (zafirlukast) Zeneca) can be administered to further prevent such an inflammatory reaction from occurring.

As previously alluded to, the products of the 5-LO metabolic pathway contemplated by the present invention are associated with additional attributes. For example, the lipid products do not elicit immunologic reactions like polypeptide agents do. Furthermore, the compounds of the present invention are relatively inexpensive, making them ideal as an adjunct to infection treatment.

The compounds contemplated by the present invention provide a means for enhancing pulmonary defense capabilities. They are especially efficacious in the treatment and prevention of bacterial pneumonia in those patients who are predisposed to that condition. Of course, the present invention contemplates the use of the compounds in the treatment and prevention of other infections and ailments, alone or in combination with, for example, other products of the 5-LO pathway or antimicrobial agents.

EXPERIMENTAL

The following examples serve to illustrate certain preferred embodiments and aspects of the present invention and are not to be construed as limiting the scope thereof.

In the experimental disclosure which follows, the following abbreviations apply: M (Molar); mM (millimolar); $\mu$M (micromolar); N (Normal); mol (moles); mmol (millimoles); $\mu$mol (micromoles); nmol (nanomoles); pmol (picomoles); g (grams); mg (milligrams); $\mu$g (micrograms); L (liters); mL (milliliters); $\mu$L (microliters); cm (centimeters); mm (millimeters); $\mu$m (micrometers); nm (nanometers); min. (minutes); s and sec. (seconds); OD (outside diameter); °C. (degrees Centigrade); v/v (volume/volume); AM (alveolar macrophage); BAL (bronchoalveolar lavage); BALF (bronchoalveolar lavage fluid); cPLA$_2$ (cytosolic phospholipase A$_2$); CFU (colony-forming unit); 5-LO (5-lipoxygenase); FLAP (5-LO activating protein); AA (arachidonic acid); LT (leukotriene); LTB$_4$ (leukotriene B$_4$); LTC$_4$ (leukotriene C$_4$); LTB$_4$R (LTB$_4$ receptor); cys-LTR (cysteinyl leukotriene receptor); CR3 (complement receptor 3); FcR (receptor for Fc portion of Ig); MPO (myeloperoxidase); PKC (protein kinase C); MAPK (Mitogen Activated Protein Kinase); O$_2$-(superoxide); NO (nitric oxide); PM (peritoneal macrophages); PMN (polymorphonuclear leukocytes); KO (knockout); WT (wild type); TNF (tumor necrosis factor); JE (the murine homologue of monocyte chemotactic peptide-1); IL (interleukin); HBSS (Hank's Balanced Salt Solution); RP-HPLC (reversed-phase high pressure liquid chromatography); SE (standard error); SEM (standard error of the mean); Abacus (Abacus Concepts, Inc., Berkeley, Calif.); Abbott (Abbott Laboratories, North Chicago, Ill.); ATCC (American Type Culture Collection; Rockville, Md.); Baxter (McGaw Park, Ill.); Biogenics (Napa, Calif.); Cayman (Cayman Chemical; Ann Arbor, Mich.); Coulter (Coulter Corp., Miami, Fla.); Difco (Detroit, Mich.); Fisher Scientific, Pittsburg, Pa.); Gibco (Gibco BRL; Gaithersburg, Md.); Jackson (The Jackson Laboratory; Bar Harbor, Me.); Merck (Rahway, N.J.); Molecular Probes (Eugene, Oreg.); Nunc (Naperville, Ill.); PharMingen (San Diego, Calif.); Pierce (Rockford, Ill.); Pfizer (Pfizer Inc., New York, N.Y.); Vector (Vector Laboratories, Burlingame, Calif.); and Waters (Waters Corp., Milford, Mass.); Zeneca (Zeneca Pharmaceuticals, Wilmington, Del.).

The following General Methods were used in the examples that follow unless otherwise indicated.

Animals

Mice with the targeted disruption of their 5-LO gene (ALOX 5, designated KO) and their wild type strain controls (129/SvEv, designated WT) were obtained from The Jackson Laboratory.

K. pneumoniae Inoculation

K. pneumoniae strain 43816, serotype 2 obtained from the ATCC (Assession No. 29939) was grown in tryptic soy broth (Difco) for 18 hours at 37° C. The preparation and intratracheal administration of K. pneumoniae were carried out as described by M. Schneemann et al. [J. Infect. Dis. 167:1358–1363 (1993)]. Bacterial concentration was determined by measuring absorbance at 600 nm and referencing to a standard curve of absorbances vs. known standard CFUs. Bacteria were then pelleted by centrifugation for 30 min at 10,000 rpm, washed×2 in saline, and resuspended at the desired concentration in saline.

After appropriate dilution of bacteria in endotoxin-free saline, animals were anesthetized with sodium pentobarbital (approximately 0.2 mL diluted 1:7 in saline intraperitoneally) and the trachea was exposed via a small midline incision. A 30 $\mu$L inoculum containing 50 CFU K. pneumoniae or saline was administered via a sterile 26-gauge needle and the skin was closed with a surgical staple. For preparation of K. pneumoniae-specific serum, wild type mice are similarly anesthetized and inoculated intratracheally (with 25 CFU bacteria); animals are bled orbitally 2 weeks later, and serum obtained.

Determination of Plasma and Lung CFU

Plasma and lung CFU were determined as described by M. Schneemann et al. [J. Infect. Dis. 167:1358–1363 (1993)]. Briefly, lungs homogenized in 3 mL sterile saline and plasma collected at euthanasia were placed on ice, and serial 1:10 dilutions made. Ten $\mu$L of each dilution were plated on soy base blood agar plates (Difco), incubated for 18 hours at 37° C., and colonies were enumerated.

Preparation and Analyses of Lung Homogenates

At 30 and 48 hours post-inoculation, mice were anesthetized and blood was collected by orbital exsanguination. The mice were then euthanized via cervical dislocation and whole lungs were harvested for the determination of cytokine levels, myeloperoxidase activity (MPO), and leukotriene levels. For cytokine and leukotriene analyses, lungs were homogenized in 2 mL of buffer containing 0.5% Triton X100, 150 mM NaCl, 15 mM Tris-HCl, 1 mM CaCl$_2$, and 1 mM MgCl$_2$. Homogenates were then centrifuged at 1500×g for 10 minutes and supernatants filtered through a 1.2 $\mu$m syringe filter and immediately frozen at −20° C. TNF, macrophage inflammatory protein-1$\alpha$, macrophage inflammatory protein-2, murine JE, and IL-12 were each quantified using a modification of a double ligand method as described by M. Schneemann et al. [J. Infect. Dis. 167:1358–1363 (1993)]. For determination of leukotriene levels in lung homogenates, samples were extracted on C$_{18}$ Sep-Pak® cartridges® (Waters) to remove potentially cross-reactive materials, and evaporated to dryness under N$_2$. [J. Wilborn et al., J. Clin. Invest. 97:1827 (1996)]. An analogous procedure is used with bronchoalveolar lavage fluid.

Samples were resuspended in assay buffer and LTB$_4$ and LTC$_4$ levels were determined according to manufacturers instructions using enzyme immunoassay kits obtained from Cayman Chemical. MPO activity, an index of neutrophil influx, was quantified in lung homogenates as described by M. Greenberger et al. [J. Immunol. 155:722 (1995)]. Briefly, lungs were homogenized in 2 mL of buffer containing 50 mM potassium phosphate, pH 6.0, with 5% hexadecyltrimethylammonium bromide and 5 mM EDTA. The homogenate was sonicated and centrifuged and the supernatant was mixed 1:15 with assay buffer (86 mM monobasic sodium phosphate, 12 mM dibasic sodium phosphate, 0.0005% [v/v] H$_2$O$_2$, and 0.167 mg/mL o-dianisidine hydrochloride) and read at 490 nm (Beckman DU-64). MPO units were calculated as the change in absorbance over time. Protein content of homogenates is determined using a microtiter plate modification (Pierce Biochemical) of the Bradford method using bovine serum albumin as a standard.

Lung Lavage

The trachea was exposed through a 0.5 cm incision and intubated using a 1.7 mm OD polyethylene catheter. Bronchoalveolar lavage was performed by instilling 1 mL aliquots of phosphate-buffered saline containing 5 mM EDTA. Approximately 4 mL of lavage fluid were retrieved per mouse, and total cell numbers and differential cell counts were determined from cytospins on each sample.

Alveolar Macrophage Culture and Functional Assays

For assays of bacterial phagocytosis and killing, alveolar macrophages were purified from bronchoalveolar lavage cells by adherence for 1 hour in HBSS and studied in monolayer culture. Adherent cells were preincubated with 5% K. pneumoniae-specific immune serum (as a source of both complement and specific opsonizing antibody) for 5 minutes at 37° C. prior to assays. Phagocytosis was studied by incubating $10^5$ alveolar macrophages with $10^6$ K. pneumoniae in each well of an 8-well Labtek® plate (Nunc) for 1 hour at 37° C.; in some experiments, exogenous LTB$_4$ (Cayman) was added concomitantly with bacteria. The supernatants were aspirated and the cells were washed 3 times with HBSS. The slides were then allowed to air dry, Diff-Quik® (Difco) staining was performed, and 200 cells per well were counted to determine number of intracellular K. pneumoniae and percent of alveolar macrophages containing bacteria. Phagocytic index was calculated as the mean percentage of alveolar macrophages containing bacteria multiplied by the mean number of bacteria per alveolar macrophage.

The bactericidal activity was assayed by incubating for 1 hour at 37° C. the same numbers of alveolar macrophages and organisms as detailed above, but in 35 mm tissue culture dishes. Supernatants were removed and cells were than washed with HBSS and lysed by adding 1 mL of cold sterile water, scraping with a rubber policeman, and incubating on ice for 10 minutes. One mL of 2×HBSS was added to each plate and lysates were serially diluted on blood agar plates. Plates were incubated for 18 hours at 37° C. and colony counts performed. Percent killing of intracellular bacteria was calculated by the following formula: 100—(number of bacterial CFU/mL alveolar macrophage lysate divided by the total number of intracellular bacteria), where total intracellular $K.$ $pneumoniae$ is the product of the total number of alveolar macrophages x the percentage of alveolar macrophages containing bacteria x the mean number of bacteria per alveolar macrophage.

Neutrophil Culture and Functional Assays

To obtain peritoneal elicited neutrophils, mice are injected intraperitoneally with 5% glycogen in PBS and peritoneal lavage is performed 5 hours later. Approximately $3\times10^6$ cells are obtained from each animal, approximately 85–90% of which are neutrophils. These cells are likewise placed into culture for functional studies. Phagocytic and bactericidal assays are performed as described above.

Lung lavage from $K.$ $pneumoniae$-challenged animals yields a mixture of alveolar macrophages and neutrophils; they are found in a ratio of approximately 1:1 at 2 days post-inoculation, but the ratio is likely to vary over time. To determine constitutive secretion of leukotrienes by these cells, mixed bronchoalveolar lavage cells are placed into culture ($5\times10^5$ cells/well) as described above for purified populations; the ratio of alveolar macrophage:neutrophil in adherent monolayers is determined by direct Diff-Quik® staining of monolayers after the removal of medium. In all instances where leukotriene levels in culture medium are quantitated, values are expressed per $\mu g$ of cell protein. Culture medium is medium 199 (Gibco).

In Vivo Administration of Anti-leukotriene Drugs and Leukotrienes

Doses of 5-LO inhibitor (A-79175; Abbott), $LTB_4$ receptor antagonist (CP-105,696; Pfizer), and cysteinyl leukotriene receptor antagonist (MK-571; Merck Research Laboratories) are suspended in methylcellulose and administered once per day orally to unanesthetized mice using a 22 gauge gavage needle.

Ethanolic stock solutions of $LTB_4$, $LTC_4$, and 5-HETE (Cayman Chemical) were diluted in saline and a 10 $\mu L$ volume used for intratracheal injection. For nebulization, a particle size <3 $\mu m$ and a nose-only exposure chamber is utilized.

Immunohistochemical Staining for 5-LO

Lung sections as well as bronchoalveolar lavage cytospins are stained for 5-LO in order to identify the frequency and types of cells exhibiting localization of enzyme to the nuclear envelope (an "activated" pattern). [J. Wilborn et al., J. Clin. Invest. 97:1827–1836 (1996)]. Briefly, specimens are fixed in 4% paraformaldehyde, embedded in paraffin, and 3-$\mu m$-thick sections cut and mounted on Superfrost/PLUS® slides (Fisher Scientific). Paraffin is removed with Americlear® (Baxter) and tissue is rehydrated. To reduce nonspecific binding, tissue is incubated with Power Block® (Biogenics) followed by 25% normal goat serum.

Sections and cytospins are incubated at 4° C. for 24 hours with either rabbit anti-human 5-LO antiserum (Merck Frosst Canada) or nonimmune rabbit serum at 1:1000 in 25% normal goat serum in PBS. This antibody also recognizes the mouse and murine 5-LO. Goat anti-rabbit IgG (1:600) is then applied for 30 minutes and primary antibody is detected using True-Blue® peroxidase substrate with Contrast Red® counterstain (both from KPL Laboratories). The proportion of positively stained cells exhibiting an activated pattern is determined from counts of 20 high power fields. Cells staining positively for 5-LO (most of which are expected to be either macrophages or neutrophils) are classified as to cell type on the basis of morphology. If necessary to distinguish alveolar macrophages and neutrophils, dual staining is undertaken. Cell type-specific staining is accomplished either with a second primary (e.g., anti-neutrophil antibody) or via histochemical staining (e.g, for nonspecific esterase or MPO). The second protein is detected by Vector Red® (Vector) to contrast with the True-Blue® stain for 5-LO.

Cell Surface Expression of CR3 and FcR Receptors

Expression of CR3 and FcR is quantitated in both alveolar macrophages and neutrophils by staining with FITC-conjugated anti-mouse monoclonal antibodies with subsequent analysis by flow cytometry. [L. Laichalk et al., FEMS Immunol. Med. Microbiol. 658:1–7 (1996)]. The FITC-conjugated monoclonal antibodies (PharMingen) include anti-CR3 $IgG_1$, anti-FcRII/FcRIII $IgG_1$, and an anti-$IgG_1$, isotype control. Experimental incubations are carried out in suspension. Five×$10^5$ cells are stained with 1 $\mu g$ of monoclonal antibody for 30 minutes on ice, washed, fixed in 2% paraformaldehyde in PBS, and stored at 4° C. in the dark until analyzed. Samples are analyzed on an EPICS C flow cytometer with accompanying software (Coulter Corp.) available at the University of Michigan Flow Cytometry Core Facility, examining at least 20,000 events per sample. After correction for staining by the control IgG, both the percentage of positively stained cells and the mean fluorescence intensity are determined.

Analysis of Actin Polymerization

Engulfment of attached particles or bacteria requires cytoskeletal rearrangement, including local actin polymerization. Polymerized actin (F-actin) is analyzed by staining with rhodamine-phalloidin (Molecular Probes) at a 1:300 dilution. Intracellular localization of F-actin is assessed by immunofluorescence microscopy. Cells on cover slips are fixed with formalin and permeabilized in acetone. [T.G. Brock et al., J. Biol. Chem. 269:22059–22066 (1994)]. Following incubation with phalloidin for 1 hour, the cells are examined with a Nikon Labophot 2 microscope equipped for epifluorescence. To quantify the total cellular content of F-actin, cells are permeabilized with 0.1% Triton X-100 and incubated with rhodamine-phalloidin and analyzed by flow cytometry. [R. Crowell et al., Am. J. Respir. Cell Mol. Biol. 12:190–195 (1995)].

Assessment of Phagosome-lysosome Fusion

Adherent cells from knockout or wild type mice are prelabeled by incubation for 15 minutes with 5 $\mu g/mL$ acridine orange (Molecular Probes). Cells are washed, pre-incubated with specific immune serum, and then incubated for up to 2 hours with $K.$ $pneumoniae$ alone or in the presence of exogenous leukotrienes. Cells are examined by immunofluorescence microscopy. Two hundred cells per condition are counted, and the percentage of cells showing fusion as well as the total number of fusion figures are recorded.

Assays for $O_2$—, and $\beta$-glucuronidase

Superoxide production by 0.5–1.0×$10^6$ adherent cells incubated with 0.5–1.0×$10^7$ $K.$ $pneumoniae$ or 100 nM phorbol myristate acetate is assessed from the superoxide dismutase-inhibitable reduction of ferricytochrome C. [L. Laichalk et al., FEMS Immunol. Med. Microbiol. 658:1–7

(1996)]. The assay is performed in 96-well plates, and read at 550 nm. NO generation is determined by quantitating nitrite, its metabolite, in L-arginine-supplemented culture medium of $10^6$ cells incubated for 2 hours with bacteria. [M. Schneemann et al., J. Infect. Dis. 167:1358–1363 (1993)]. Medium is centrifuged to remove bacteria, and supernatants added to Griess reagent (0.05% N-1-naphthylethylenediamine dihydrochloride, 0.5% sulfanilamide, 2.5% phosphoric acid) and incubated in 96-well plates for 10 minutes; absorbance is read at 570/630 nm. The lysosomal enzyme β-glucuronidase is quantitated in medium and cell lysates [W. Hsueh et al., Exp. Lung Res. 13:385–399 (1987)] using the reagent 4-methyl umbelliferyl β-D-glucuronide trihydrate; fluorescence is read at 375/455.

Statistical Analysis

Data were analyzed using The Statview II® statistical package (Abacus Concepts). Comparisons for survival data were made using the Chi-square analysis. All other data are expressed as mean±SEM. Comparisons between treatment means were carried out using a two-tailed Student's t-test or the Wilcoxen rank sum test, as appropriate (i.e., depending on whether data is parametric or non-parametric). For comparisons of mean data from three or more experimental groups, ANOVA and subsequent application of the Newman-Keuls test is used. The criterion for significance was $p \leq 0.05$.

EXAMPLE 1

Survival Following Intratracheal Klebsiella Challenge In 5-LO Knockout Mice and Wild Type Mice Intratracheal instillation of *K. pneumoniae* in mice is known to cause a reproducible pneumonia characterized by acute pulmonary inflammation that, depending on the inoculum, either resolves or results in death. [G. Rosen et al., FASEB J. 9:200–209 (1995)]. To assess the role of 5-LO products in pulmonary host defense, this example compares the survival of 5-LO knockout and wild type mice.

Profiles of Eicosanoids

Figure 2A:
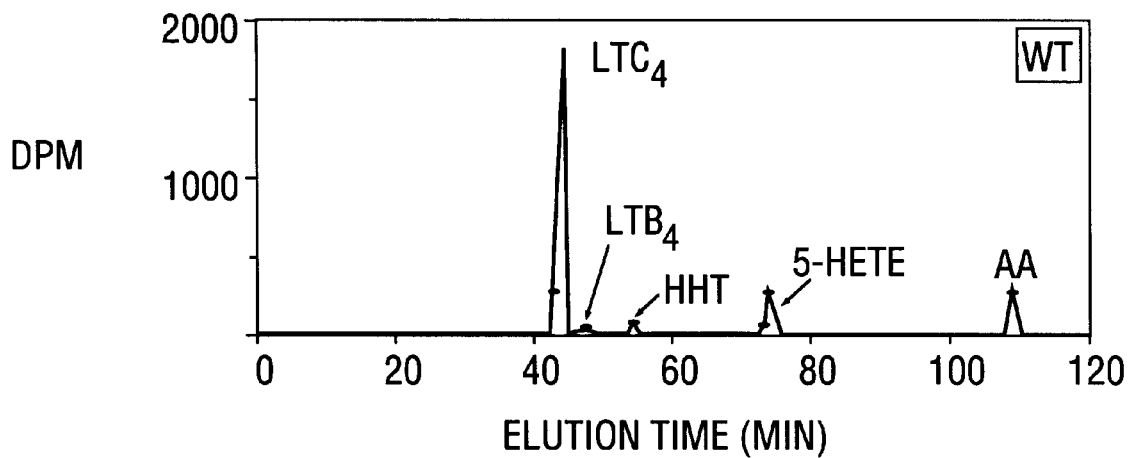
FIGS. 2A and B depict RP-HPLC profiles of radioactive eicosanoids released by prelabeled alveolar macrophages obtained from wild type mice (FIG. 2A) and 5-LO knockout mice (FIG. 2B).
Figure 2B:
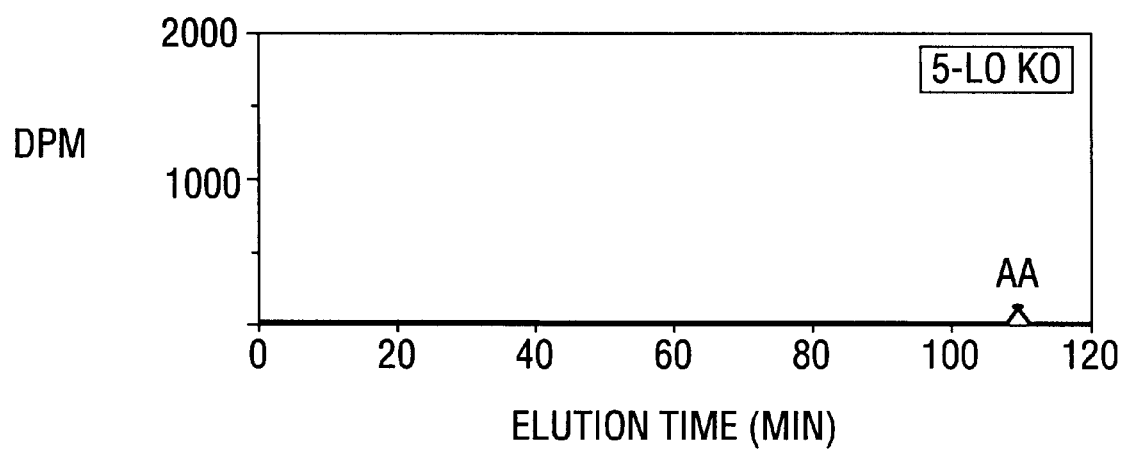

FIGS. 2A and B depict RP-HPLC profiles of radioactive eicosanoids released by prelabeled alveolar macrophages obtained from wild type mice (FIG. 2A) and 5-LO knockout mice (FIG. 2B). The profiles were obtained by prelabeling $10^6$ alveolar macrophages overnight with [$^3$H]arachidonic acid. The alveolar macrophages were then washed and stimulated for 30 minutes with 1 μM A23187. The medium was subjected to lipid extraction and radiolabeled eicosanoids separated by reverse-phase HPLC. Peaks were identified on the basis of co-elution with authentic standards. As compared to cells from wild type control animals (FIG. 2A), alveolar macrophages from KO animals produced no leukotrienes or 5-HETE, as expected. Moreover, there is no increased production of prostaglandins from a possible "shunting" of acrachidonic acid. This indicates that any reduction in antimicrobial defense in these animals is likely attributable to their deficiency of pro-inflammatory leukotrienes, rather than to an overproduction of anti-inflammatory prostaglandin $E_2$.

Mouse Survival

Figure 3:
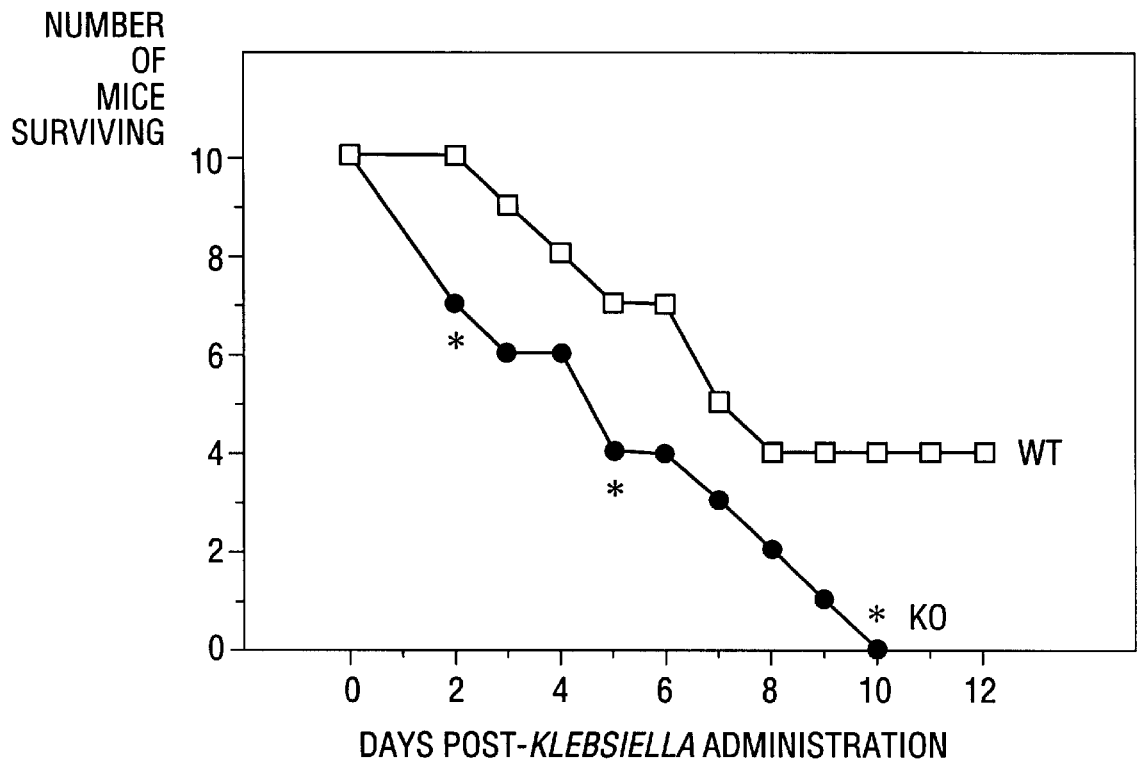
FIG. 3 graphically depicts the effect of *Klebsiella pneumoniae* challenge on survival in 5-LO knockout mice and wild type mice.

For this experiment, 5-LO knockout mice and strain-matched (129/SvEv) wild type mice (ten animals per group) were inoculated intratracheally with 50 CFU of bacteria, and survival was monitored over a 12-day period. FIG. 3 graphically depicts the effect of *K. pneumoniae* challenge on survival in 5-LO knockout mice (solid circles) and wild type mice (open squares) ($^*p<0.05$ vs. WT). As the results in FIG. 3 indicate, administration of 50 CFU of bacteria led to 60% mortality in wild type mice within 8 days, with no subsequent deaths thereafter. In contrast, all of the knockout mice died in response to this same challenge, with all deaths occurring by day 10. Moreover, deaths in the knockout group occurred earlier than in the wild type animals.

These results indicate that the metabolic products of 5-LO play an important role in the protective host response in this model of pneumonia. The importance of early events following bacterial challenge is indicated by the fact that the survival curves in FIG. 3 diverge as early as day 2.

EXAMPLE 2

Bacterial Clearance Following Intratracheal Klebsiella Challenge In 5-LO Knockout Mice and Wild Type Mice As set forth in the preceding example, early events following bacterial challenge (i.e., approximately two-days post-challenge) are important. This example further explores those results by assessing lung homogenate and plasma CFUs at 30 and 48 hours after *K. pneumoniae* administration.

Figure 4:
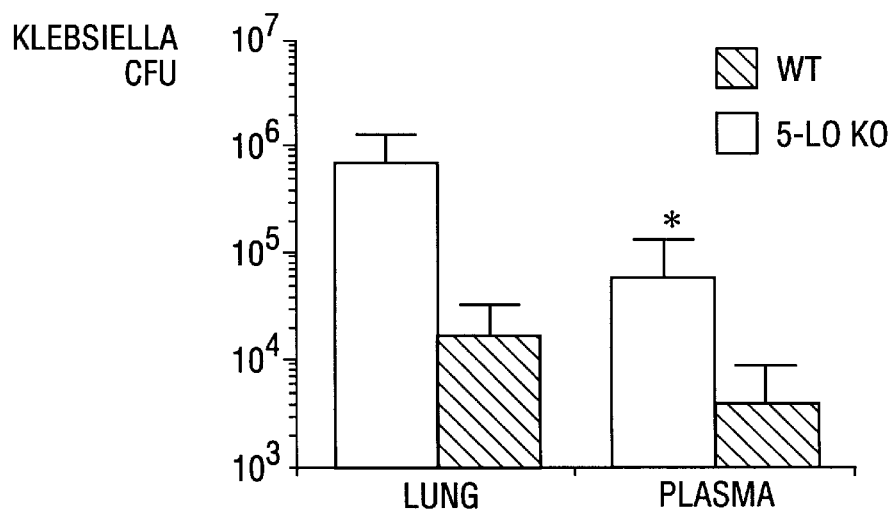
FIG. 4 graphically depicts the clearance of *K. pneumoniae* from lung and plasma two days after challenge in 5-LO knockout and wild type mice.

Knockout mice and wild type mice were inoculated with 50 CFU intratracheally, and lung homogenate levels and plasma CFU values were determined 48 hours later. FIG. 4 graphically depicts the clearance of *K. pneumoniae* from lung and plasma after challenge in 5-LO knockout mice (cross-hatched bars) and wild type mice (solid bars) (bars represent mean±SE; n=5–19 animals; $^*p<0.05$ vs. WT). As indicated by the data in FIG. 4, mean lung as well as plasma CFUs were almost two logs greater in knockout mice than in wild type mice at 48 hours post-challenge. Furthermore, the proportion of knockout animals that developed bacteremia at this time point (15/19) was significantly greater than that of wild type mice (10/19). In an additional group of animals studied at 30 hours post-challenge, 66% of knockout mice were bacteremic (average plasma CFU of $1.06 \times 10^5$), while no wild type mice had bacteria in their plasma at this time point (data not shown).

These data confirm the importance of an intact leukotriene-generating system for the early containment of a pulmonary challenge with *K. pneumoniae*.

EXAMPLE 3

Effect Of Leukotriene Deficiency And Exogenous Leukotrienes On Alveolar Macrophage Antibacterial Functions In Vitro The experiments of this example assess the ability of the alveolar macrophages themselves, the first line of cellular defense, to phagocytose and kill *K. pneumoniae* in vitro and the effect of administering exogenous leukotrienes on alveolar macrophage antibacterial functions in vitro.

Phagocytic and Bactericidal Activities of Alveolar Macrophages from 5-LO Knockout and Wild Type Mice Alveolar macrophages were purified by adherence of bronchoalveolar lavage cells lavaged from uninfected knockout and wild type animals, and preincubated for 5 minutes with 5% *K. pneumoniae*-specific immune serum (as a source of both complement and specific opsonizing antibody) prior to assays. Cultured alveolar macrophages from either group of mice were incubated in the presence of specific serum with *K. pneumoniae* for 1 hour and then washed, after which monolayers were either stained with Diff-Quik (Difco) and intracellular organisms enumerated, or lysed and bacterial CFUs in lysates determined following overnight culture. Phagocytic index and intracellular killing were calculated as detailed above in General Methods.

Figure 5:
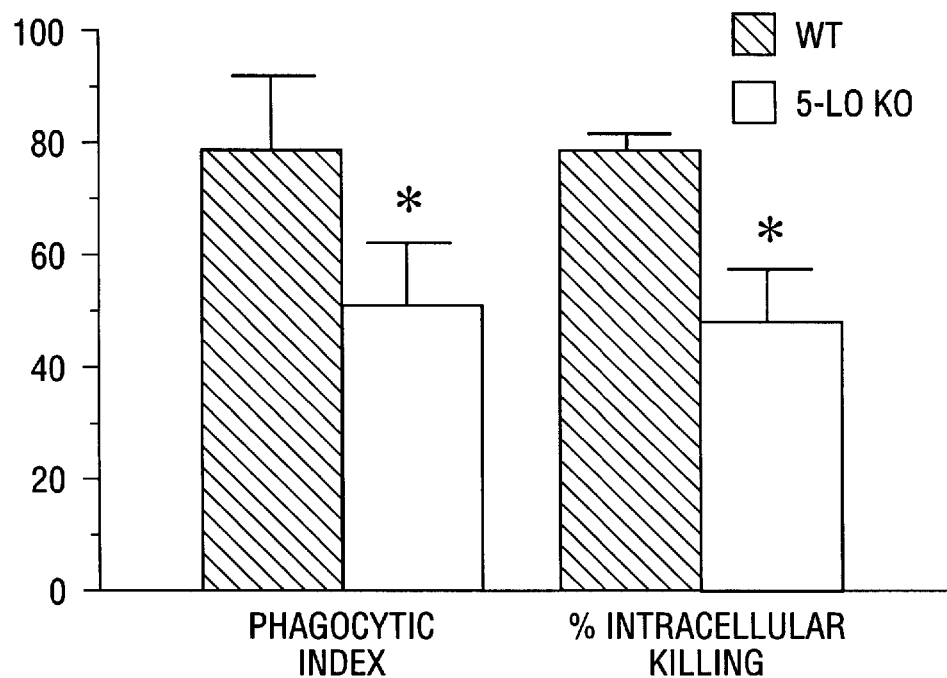
FIG. 5 graphically depicts phagocytic and bactericidal activities in alveolar macrophages from 5-LO knockout and wild type mice.

FIG. 5 graphically depicts phagocytic and bactericidal activities in alveolar macrophages isolated from 5-LO knockout mice (cross-hatched bars) and wild type mice (solid bars); in FIG. 5, each value represents the mean±SEM of 6 replicate cultures (*p<0.05 vs. WT). As indicated by the data in FIG. 5, alveolar macrophages from 5-LO knockout mice demonstrated significant decreases in their abilities to both ingest and kill *K. pneumoniae* when compared to cells from wild type mice. Since killing of microbes depends on their prior ingestion, the magnitude of the host defense defect in alveolar macrophages from knockout animals reflects the arithmetic product of these two individual defects and amounts to approximately a 60% reduction in microbial killing under the conditions employed. Though exogenous $LTB_4$ has previously been reported to enhance Gram-negative bacterial killing by macrophages in vitro and bacterial clearance in vivo [T. Demitsu et al., Int. J. Immunopharmac. 11:801–808 (1989)], the data set forth above indicate an important role for endogenous 5-LO products in these same processes in vivo and in vitro.

Effect of Exogenous $LTB_4$ on Bacterial Phagocytic Activity of Alveolar Macrophages from 5-LO Knockout and Wild Type Mice Further experiments were performed to determine whether defective phagocytosis of *K. pneumoniae* in alveolar macrophages from 5-LO knockout animals could be overcome by the addition of exogenous $LTB_4$. This particular leukotriene was selected because, as previously indicated, its leukocyte-activating properties have been well-characterized.

Figure 6:
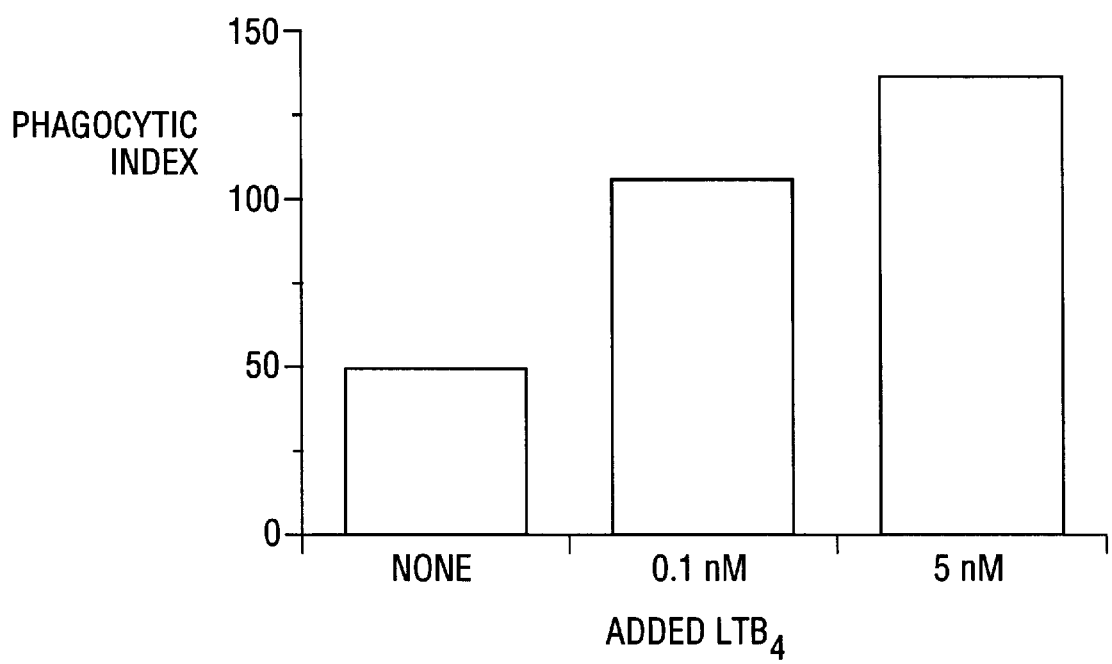
FIG. 6 graphically depicts the effect of exogenous $LTB_4$ on bacterial phagocytic activity in alveolar macrophages from 5-LO knockout mice.

Cultured alveolar macrophages from knockout mice were incubated in the presence of specific serum for 1 hour with *K. pneumoniae* alone or in the presence of varying doses of $LTB_4$. Phagocytic index was calculated as described in the General Methods. FIG. 6 graphically depicts the effect of exogenous $LTB_4$ (none, 0.1 nM, and 5 nM $LTB_4$ added) on bacterial phagocytic activity in alveolar macrophages from 5-LO KO mice; each value represents the mean from triplicate cultures. As shown in FIG. 6, $LTB_4$ dose-dependently enhanced the phagocytic index in knockout alveolar macrophages, with an index approximately three times the baseline level at a concentration of 5 nM. Though not required in order to practice the present invention, it is believed that neutrophils manifest similar functional defects in phagocytosis and killing which could contribute to the sensitivity to bacterial pneumonia seen in knockout mice in vivo.

The effects of exogenous $LTB_4$ on phagocytosis by neutrophils from 5-LO knockout mice were also examined. Glycogen-elicited neutrophils were obtained from the peritoneal cavity of knockout mice, and phagocytosis of *K. pneumoniae* over a one hour time period was evaluated in the presence and absence of exogenous $LTB_4$ (1 nM); under these circumstances, phagocytic index was 27±8 and 45±4, respectively (data not shown). These results with exogenous $LTB_4$ are important in several respects. First, they indicate that the phagocytic defect in these cells is actually related to the deficiency of 5-LO, and is not coincidental. Second, the fact that addition of exogenous leukotriene could overcome the lack of 5-LO indicates that the functional defect in these cells was causally related to their endogenous leukotriene deficiency; this finding is contrary to the findings of other researchers who found that functional defects in leukocytes caused by 5-LO inhibitors could not be overcome by addition of exogenous leukotrienes. [See, e.g., N. Hubbard and K. Erickson, Mol. Immunol. 160:115–122 (1995)]. Third, the rapidity of the enhancement of phagocytic capacity produced by the addition of exogenous leukotriene indicates that this effect might be reproduced by pulmonary delivery of this lipid in vivo; such a rapid increase in bacterial clearance has been observed upon injection of $LTB_4$ into the peritoneum in vivo. [T. Demitsu et al., Int. J. Immunopharmac. 11:801–808 (1989)].

EXAMPLE 4

Inflammatory Cells And Mediators Following Intratracheal Klebsiella Challenge In 5-LO Knockout Mice and Wild Type Mice This example evaluates the mechanisms responsible for the enhanced susceptibility of knockout mice to Klebsiella pneumonia. Of course, it is to be understood that an understanding of the mechanisms is not required in order to practice the present invention.

Figure 7:
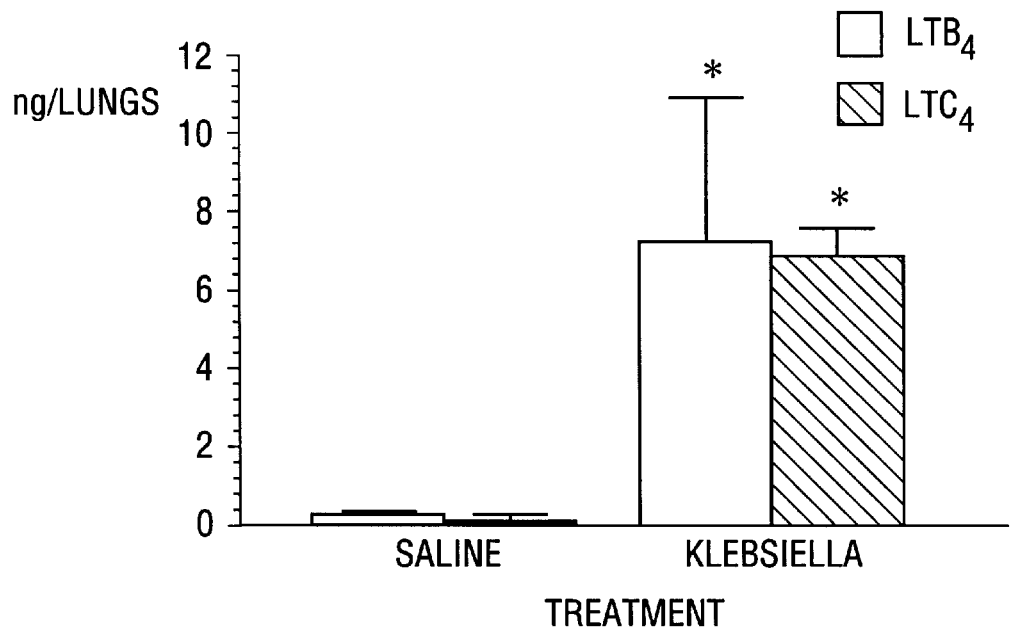
FIG. 7 graphically depicts lung homogenate levels of $LTB_4$ and $LTC_4$ in wild type mice two days after challenge with either *K. pneumoniae* or saline.

Wild type mice were injected intratracheally with either 50 CFU of bacteria (*Klebsiella pneumoniae*) or saline diluent alone. Two days later, lungs were harvested and homogenized. The homogenates were subjected to lipid extraction, and immunoreactive leukotrienes $B_4$ and $C_4$ were quantitated. FIG. 7 graphically depicts lung homogenate levels of $LTB_4$ (hatched bars) and $LTC_4$ (solid bars) after challenge with either *K. pneumoniae* or saline (values represent mean±SEM; n=5 animals; *p<0.05 vs. saline).

Figure 8:
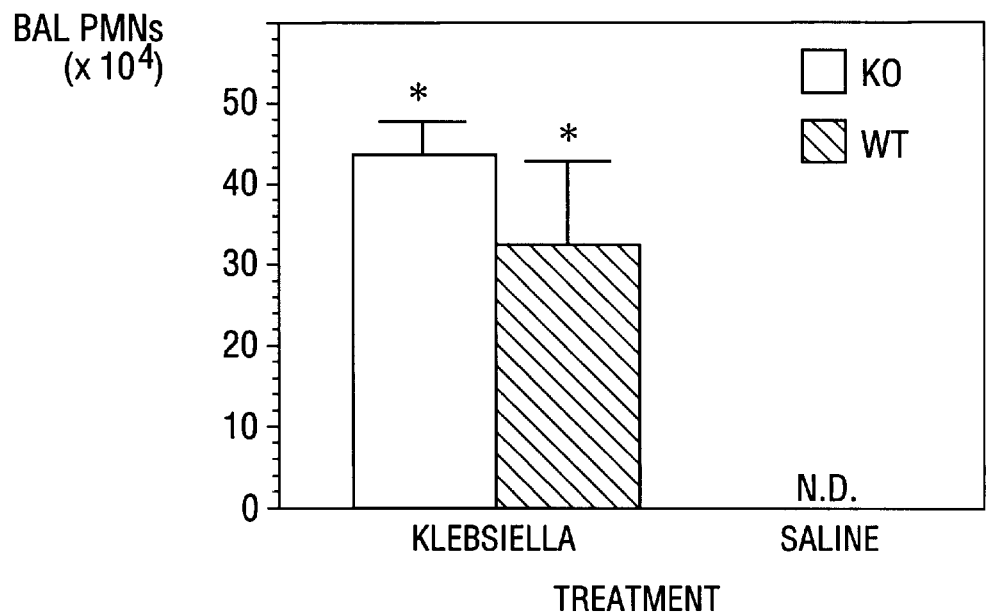
FIG. 8 graphically depicts the effect of *K. pneumoniae* challenge on lavage neutrophilia in 5-LO knockout and wild type mice.

As the results in FIG. 7 illustrate, both leukotriene $B_4$ and $C_4$ levels were elevated in the lung homogenates of wild type mice 48 hours after challenge with bacteria as compared to saline. As $LTB_4$ is a potent neutrophil chemotaxin in mice and neutrophil recruitment is considered an essential component of bacterial clearance, the presence of high levels of $LTB_4$ in lungs of bacteria-challenged wild type animals indicates that the enhanced susceptibility to pneumonia in knockout animals might reflect a reduced capacity to recruit neutrophils to the infected organ. In order to evaluate that possibility, direct counts of bronchoalveolar lavage neutrophils from cytospins (FIG. 8) were performed and lung homogenate MPO activity was spectrophotometrically assayed (not shown) [M. Greenberger et al., J. Immunol. 155:722–729 (1995)]. Knockout and wild type mice were inoculated intratracheally with either 50 CFU of bacteria or saline diluent alone. Two days later, lung lavage was performed and the total neutrophil count was determined. FIG. 8 graphically depicts the effect of *K. pneumoniae* challenge on lavage neutrophilia in 5-LO knockout (cross-hatched bars) and wild type (solid bars) mice (values represent mean±SEM; n=3–12 animals; *p<0.05 vs. saline; ND, none detected).

Both techniques indicated that a significant degree of neutrophil influx occurred at 48 hours in bacteria-challenged as compared to saline-challenged wild type lungs. Surprisingly, however, knockout mice exhibited no less neutrophil influx following bacterial challenge than did wild type mice.

Though the precise mechanism is not required to practice the present invention, experiments were performed to determine whether the intact capacity for neutrophil recruitment in this murine model reflects a compensatory increase in the knockout animals to generate alternative chemotactic signals such as chemokines. An evaluation of antigenic MIP-1α, MIP-2, and JE (the murine homologue of monocyte chemotactic peptide-1) levels in homogenates of Klebsiella-challenged lungs at this same time point (i.e., 48 hours post-challenge) disclosed no significant differences between knockout and wild type mice (data not shown). Alternatively, while an understanding of the mechanism is not required in order to practice the present invention, it is possible that the knockout animals might exhibit increased generation of complement components or increased responsiveness to chemokines or bacterial chemotaxins.

Although not directly chemotactic, both IL-12 and TNF have been shown to play critical protective roles in this model of murine pneumonia. Additionally, TNF production is potentiated by leukotrienes in some experimental systems. To examine the possibility that the enhanced susceptibility of knockout mice to bacterial challenge might relate to an impaired ability to generate either of these cytokines, lung homogenates were analyzed 48 hours after bacterial challenge. Again, no significant differences were found in antigenic IL-12 or TNF levels between infected knockout and wild type mice (data not shown). Thus, the increased lethality of pneumonia in 5-LO knockout mice does not reflect diminished capacity to produce these proinflammatory cytokines.

EXAMPLE 5

Effect of Exogenous Leukotrienes on Alveolar Macrophage Antibacterial Functions In Vitro As reported above, exogenous $LTB_4$ increased the phagocytic index of 5-LO knockout alveolar macrophages by approximately 300%, more than would have been necessary to merely attain the control level manifested by wild type cells (approximately 50% increase). That result indicates that the leukotriene is exhibiting a pharmacological effect. The experiments of this example further evaluate the effects of exogenous $LTB_4$ on phagocytic capacity of normal alveolar macrophages and examine the effects of other 5-LO products besides $LTB_4$.

Alveolar macrophages from Wistar rats were adhered and then incubated for 1 hour with *K. pneumoniae* alone or in the presence of 1 nM of several 5-LO metabolites ($LTB_4$, $LTC_4$, and 5-HETE). Phagocytic index was subsequently determined as described above in the General Methods.

Figure 9:
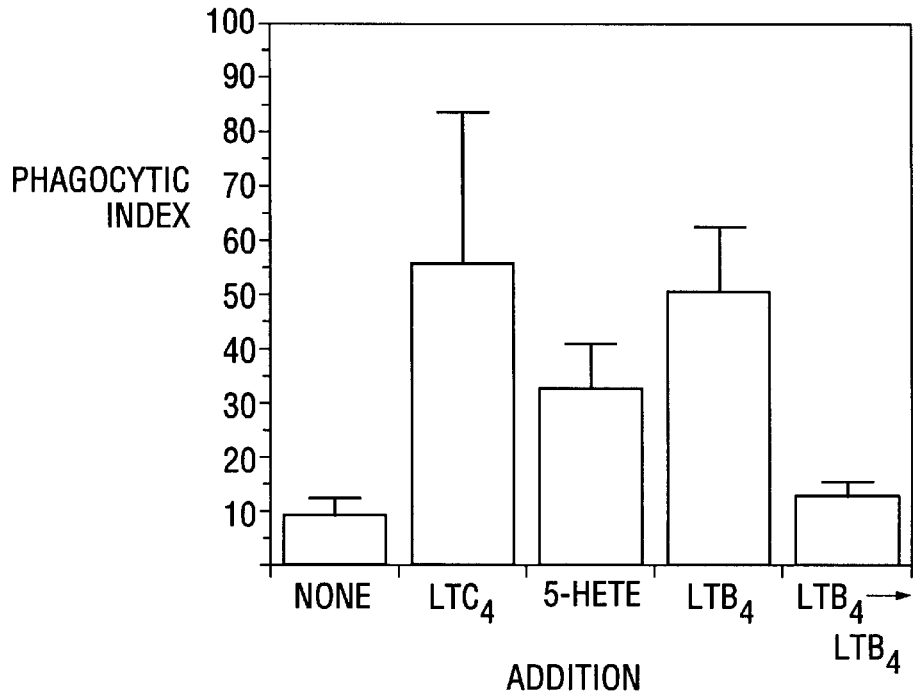
FIG. 9 graphically depicts the effect of exogenous 5-LO metabolites on bacterial phagocytic activity in normal rat alveolar macrophages.

FIG. 9 graphically depicts the effect of the exogenous 5-LO metabolites on bacterial phagocytic activity in normal rat alveolar macrophages. Each value in FIG. 9 represents the mean±SEM of 4 replicate cultures. As the data indicate, $LTB_4$ evoked an approximately 6-fold increase in phagocytic index in normal rat alveolar macrophages. The metabolite 5-HETE had a similar, though less pronounced, effect. Interestingly, $LTC_4$ augmented phagocytosis to a degree similar to $LTB_4$. Although cysteinyl leukotrienes like $LTC_4$ have been observed to upregulate surface FcR expression in macrophages, increased phagocytic capacity has not been noted previously. These results indicate that the exogenous leukotrienes as a group appear to have a marked pharmacologic effect on normal alveolar macrophage function.

A related experiment was also performed to determine if the ability of exogenous $LTB_4$ to enhance bacterial phagocytosis is mediated by its interaction with $LTB_4$ receptors. This experiment was based on the fact that pretreatment with $LTB_4$ desensitizes cells to subsequent $LTB_4$ responsiveness; though an understanding of the mechanism of this effect is not required to practice the present invention, the desensitization is believed to occur by down-regulating receptor expression or coupling. For this experiment, cells were pretreated with $LTB_4$ (1 nM) for 1 hour, washed, and incubated with bacteria plus $LTB_4$.

The results, graphically depicted by the bar labelled "$LTB_4 \rightarrow LTB_4$" in FIG. 9, indicate that pre-treatment with $LTB_4$ almost completely abrogated the ability of this same dose of $LTB_4$ (1 nM) to augment phagocytosis of *K. pneumoniae* when added simultaneously with bacteria. The findings indicate that $LTB_4$ receptors are involved in the enhancement of alveolar macrophage phagocytosis induced by $LTB_4$.

EXAMPLE 6

Effect Of Intratracheal $LTB_4$ Administration On Pulmonary Bacterial Clearance By Knockout Mice Because it was found that 5-LO knockout mice displayed reduced pulmonary clearance of *K. pneumoniae* in vivo, and exogenous leukotrienes were able to overcome the in vitro phagocytic defect observed in alveolar macrophages from knockout mice, an experiment was performed to evaluate the effect of intrapulmonary administration of leukotriene on bacterial clearance in vivo.

$LTB_4$ was administered together with the intratracheal inoculum of *K. pneumoniae* (50 CFU). A dose of 6 ng of $LTB_4$ intratracheally per animal was chosen for two reasons. First, other researchers previously found that this dose and route resulted in a brisk neutrophil influx 6 hours after administration in mice. [N. Ahmed et al., Am J. Respir. Crit. Care Med. 153:1141–1147 (1996)]. Second, the present inventors previously found (see FIG. 5) that approximately 7 ng of total $LTB_4$ could be measured in the homogenate of a pair of lungs from Klebsiella-challenged wild type mice. Three groups of animals were challenged intratracheally with bacteria (n=4 animals per group): i) wild type mice, ii) 5-LO knockout mice, and iii) 5-LO knockout mice treated concomitantly with $LTB_4$. Following 24 hours of bacterial inoculation, lungs were harvested and lung homogenate CFUs were determined.

Figure 10:
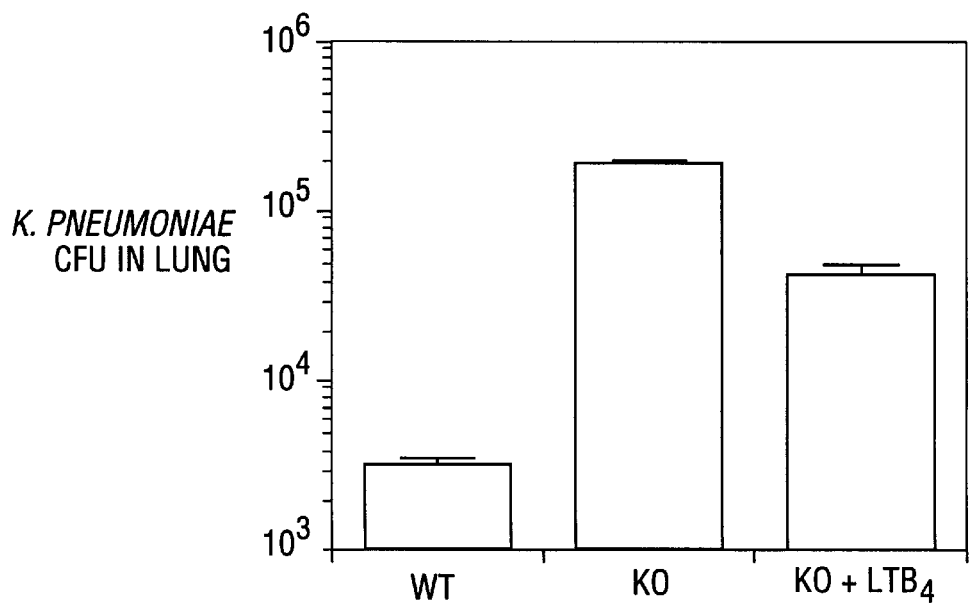
FIG. 10 graphically depicts the effect of intratracheal administration of $LTB_4$ on defective bacterial clearance of the lung in 5-LO knockout mice.

FIG. 10 graphically depicts the effect of intratracheal administration of $LTB_4$ on defective bacterial clearance of the lung in 5-LO knockout mice (each value represents the mean±SEM). The data shown in FIG. 10 confirm the previous finding (FIG. 4) that knockout mice had approximately 100-fold more organisms in their lungs than did wild type animals; it should be noted that the absolute CFUs in this experiment were less because analysis was performed at 24 hours after inoculation rather than 48 hours. Importantly, the single intratracheal dose of $LTB_4$ administered concomitantly with the bacterial inoculum reduced the lung CFU by approximately 10-fold in knockout mice. The results indicate that exogenous $LTB_4$ is capable of augmenting pulmonary clearance of *K. pneumoniae* in these leukotriene-deficient mice. Moreover, they indicate that leukotrienes should be effective therapeutic agents in the setting of Gram-negative pneumonia.

EXAMPLE 7

The Roles And Mechanisms Of Action Of 5-LO Products In The Host Response To *K. pneumoniae*

The examples described above employing intratracheal Klebsiella challenge in 5-LO knockout mice demonstrate that the enzyme plays an in vivo role in pulmonary antibacterial host defense. The experiments of this example are directed at ascertaining the roles and mechanisms of action of 5-LO products in the host response to *K. pneumoniae* using knockout mice as well as mice treated with pharmacological agents which inhibit leukotriene synthesis or actions. More specifically, the experiments of this example are directed at discerning the role of $LTB_4$ vs. cysteinyl leukotrienes by comparing the effects of a variety of pharmacologic agents, including those which target both classes of leukotrienes (5-LO inhibitor), those which target only $LTB_4$ ($LTB_4$ receptor antagonist), and those which target only cysteinyl leukotrienes (cysteinyl leukotriene receptor antagonists).

The murine model involving intratracheal challenge of mice with 50 CFU of *K. pneumoniae* is utilized in the experiments of this example. In order to pharmacologically interfere with leukotriene synthesis or action, wild type mice are treated with various long-acting agents (set forth below) by the oral (gavage) route, with daily dosing commencing the morning of the day before the administration of bacteria. In all cases, the specificity of the agents to be used has been established, and the selection of doses and dosing regimens is guided by published experience in rodents. On the basis of preliminary dose-response experiments employing three doses per agent and n=4 animals per dose, a single maximally effective dose of each drug is determined from assessments made at 24 hours after initiation of treatment.

The specific agents and preliminary dose ranges which are tested include the following: i) the 5-LO inhibitor A-79175 (Abbott) in a 1–3 mg/kg dose; this is a competitive enzyme inhibitor that is a more potent and longer-acting congener of Zileuton® with demonstrated efficacy in mice as a once-daily oral agent; ii) the $LTB_4$ antagonist CP-105,696 (Pfizer) in a 1–10 mg/kg dose; this compound has inhibited collagen-induced arthritis in mice when administered in a once-daily oral dose; and iii) the $LTD_4$ antagonist MK-571 (Merck) in a 0.1–1 mg/kg dose; this compound has effectively inhibited antigen-induced bronchoconstriction when administered orally to rats.

Once the optimal dose of each agent is defined, survival and bacterial clearance experiments are performed separately, each involving *K. pneumoniae* challenge of the following five groups of mice (n=10 per group): i) wild type mice treated with vehicle; ii) wild type mice treated with the 5-LO inhibitor; iii) wild type mice treated with the $LTB_4$ antagonist; iv) wild type mice treated with the cysteinyl leukotriene antagonist; and v) 5-LO knockout mice treated with vehicle. In vivo efficacy is judged by the following criteria. 5-LO inhibition is evaluated by quantitating pulmonary production of $LTB_4$ (quantitated in lung lavage fluid) following intratracheal instillation of ionophore A23187 in drug-treated animals. [W. Smith et al., J. Pharmacol. Exp. Ther. 275:1332–1338 (1995)]. $LTB_4$ antagonism is assessed by quantitating the ex vivo $LTB_4$-stimulated upregulation of CR3 expression on neutrophils in whole blood obtained from drug-treated animals. Cysteinyl leukotriene receptor antagonism is assessed by quantitating Evans blue dye extravasation following intradermal administration of $LTD_4$. [J. Drazen et al., Proc. Natl. Acad. Sci USA 77:4354–4358 (1980)].

Animal survival is monitored until death or until day 14. For bacterial clearance, bacterial CFU is determined in whole lung homogenates and plasma obtained from animals sacrificed at both 1 day and 3 days post-Klebsiella challenge. Finally, lung neutrophil influx is initially assessed by MPO activity of whole lung homogenates from the same animals used for CFU determinations above; if MPO assays suggest that active drug treatment results in a reduction in neutrophil influx, an additional experiment is carried out (since lavage and homogenization cannot be performed in the same animal) in which such an effect is verified by bronchoalveolar lavage cell counts and differentials on drug- vs. vehicle-treated animals.

It should be noted that determining the relative contribution to host defense of endogenously synthesized $LTB_4$ versus $LTC_4$ allows i) the design of therapeutic studies employing administration of exogenous leukotrienes and ii) the assessment of possible risks to infection susceptibility of, for example, 5-LO inhibitors (which inhibit synthesis of $LTB_4$ and cysteinyl leukotrienes in parallel) and cysteinyl leukotriene receptor antagonists (which selectively inhibit the actions of cysteinyl leukotrienes without affecting those of $LTB_4$).

If direct inhibition of 5-LO impairs survival and bacterial clearance in this murine pneumonia model in a manner similar to 5-LO deficiency, the relative roles of endogenous $LTB_4$ vs. cysteinyl leukotrienes are assessed by the application of receptor antagonists which selectively block the actions of these two groups of mediators. Although $LTB_4$ is the 5-LO metabolite most generally implicated in leukocyte-dependent inflammatory reactions, previously generated phagocytosis data suggest that cysteinyl leukotrienes might have comparable enhancing effects. Conversely, if anti-leukotriene agents do not reproduce the effects of the 5-LO gene deficiency, it will suggest that 5-LO enhances antibacterial defense by a mechanism independent of its catalytic activity. If pharmacologic inhibitors/antagonists do impair host defense, a determination is made as to whether the relevant mechanism is independent of impairment of neutrophil recruitment to the lung. Finally, the possibility that anti-leukotriene therapy augments the host response to Klebsiella pneumonia (i.e., leukotrienes both enhance and impair the host response) is considered. Indeed, results indicating that each of these opposing effects predominates at different phases of the response may warrant the use of the pharmacologic agents employed at specific intervals.

EXAMPLE 8

The Kinetics, Profile, and Cellular Sources of Leukotrienes Produced in the Murine Lung During the Course of Klebsiella Pneumonia Experiments described in previous examples (see, e.g., FIG. 3) indicated that both $LTB_4$ and $LTC_4$ are present at high levels in lung homogenates 48 hours after bacterial challenge. The experiments in this example are directed at determining which leukotrienes are produced in the lung at different time points following *K. pneumoniae* challenge and which cell types are responsible. The initial experimental objective is to quantitate leukotrienes in lung homogenates and bronchoalveolar lavage fluid from mice at various time points post-Klebsiella challenge. On the basis of these data, time points are selected for further studies designed to determine the cellular sources of leukotrienes through i) immunohistochemical staining in order to identify cells exhibiting an intracellular distribution of 5-LO associated with enzyme activation, and ii) measuring constitutive leukotriene production by cells isolated from pneumonic lungs.

Initially, 129/SvEv wild type mice are inoculated intratracheally with either saline or with 50 CFU of *K. pneumoniae*, and lungs are harvested at 8 hours and 1, 2, 3, 5, and 7 days post-inoculation. For each of these time points following saline or bacteria innoculation, whole lung homogenates are prepared (n=5 animals per group) and both $LTB_4$ and $LTC_4$ are quantitated in homogenates by immunoassay. In other animals (n=3), lung sections are prepared for immunohistochemistry (see below). In parallel, an identical experiment is conducted in which lung lavage is performed; at each time point (n=5 animals per group), bronchoalveolar lavage cytospins are prepared and levels of leukotrienes are determined in cell-free lavage fluid. Levels of $LTB_4$ and $LTC_4$ in lavage fluid and in lung homogenates are correlated with each other and with the degree of neutrophil influx (assessed from MPO activity in homogenates and cell counts and differentials from bronchoalveolar lavage fluid cytospins).

The cellular sources of leukotriene production in the lung is determined on the 8 hour, 1 day, and 3 day time points and other time points identified by the above kinetic analysis indicating maximal levels of leukotrienes $B_4$ or $C_4$. Immunohistochemical staining for 5-LO is performed on lung sections along with bronchoalveolar lavage cytospin preparations from both Klebsiella- and saline-challenged mice in order to determine whether it is the alveolar macrophages, neutrophils, or both cell types which demonstrate an intracellular distribution of 5-LO characteristic of enzyme activation (i.e., staining concentrated at the nuclear envelope). Determining 5-LO activation in lung tissue in situ by this method has the advantage that it does not require cell isolation or culture, obviating concerns about the potential artifacts which might be introduced by those procedures. Of note, this approach has been used in idiopathic pulmonary fibrosis to demonstrate that alveolar macrophages isolated by bronchoalveolar lavage from patients with idiopathic pulmonary fibrosis constitutively overproduce leukotrienes when placed into culture, even in the absence of an exogenous agonist. [J. Wilborn et al., J. Clin. Invest. 97:1827–1836 (1996)].

As described above, there is overproduction of leukotrienes in lung tissue at 2 days following bacterial challenge. In order to determine whether bronchoalveolar cells from bacteria-inoculated animals continue to elaborate leukotrienes after being placed into culture in a manner which reflects their prior generation in vivo, unfractionated bronchoalveolar lavage cells ($10^6$ cells) are obtained at the time points mentioned above, plated in culture dishes, and cumulative production of leukotrienes $B_4$ and $C_4$ are assessed by immunoassay of culture medium following overnight (approximately 16 hours) culture; bronchoalveolar lavage cells from control animals are studied for comparison (n=5 animals per treatment per time point). Following overnight culture, adherent cell differentials are determined by Wright's and esterase staining.

It should be noted that studying mixed cell populations should not create difficulty in attributing leukotriene generation to a particular cell type at the 8 hour time point because there is a relatively pure population of alveolar macrophages at the time. Furthermore, alveolar macrophages and neutrophils synthesize unique profiles of leukotriene products; thus, alveolar macrophages produce primarily $LTC_4$ (FIG. 2A) while neutrophils synthesize primarily $LTB_4$. When interpreted in conjunction with the immunohistochemical data, the profile of leukotrienes elaborated by cultured bronchoalveolar lavage cells provides strong evidence for the involvement of each cell type. Finally, studying mixed lavage cells allows potential neutrophil-alveolar macrophage interactions in leukotriene synthesis to take place, as they inevitably do in vivo.

Knowledge of the kinetics of endogenous production of $LTB_4$ vs. $LTC_4$ is helpful in several important respects. First, it provides guidance in designing the "therapeutic" experiments (described below) involving pulmonary administration of exogenous leukotrienes. Second, determining the contributions of alveolar macrophages and neutrophils as sources for the production of these mediators provides basic information about the biology of the host response. Finally, knowledge of the appropriate cellular sources of leukotrienes in the setting of bacterial pneumonia has potential diagnostic utility in that documenting deficient leukotriene production may help to identify patients who may be candidates for exogenous pulmonary leukotriene supplementation in order to augment innate immunity.

EXAMPLE 9

The Molecular Mechanisms by Which Specific 5-LO Products Augment Phagocytosis and Killing of *K. Pneumoniae* in Alveolar Macrophages and Neutrophils The experiments of this example elucidate the molecular mechanisms by which specific 5-LO metabolites enhance phagocytosis and killing. More specifically, the experiments of this example involve adding different lipids to alveolar macrophages and elicited neutrophils obtained both from knockout mice and from wild type mice in order to compare the magnitude of effects and mechanisms of action for different 5-LO products in both cell types. These experiments provide a means of i) further evaluating the therapeutic utility of leukotrienes, and ii) evaluating the utility of particular molecular and/or biochemical markers as endpoints to be examined in the in vivo leukotriene treatment studies described below in Example 10.

As described in detail hereafter, initial experiments characterize the effects of in vitro incubation with exogenous 5-LO products on the crude endpoints of phagocytosis and killing of *K. pneumoniae*. Though an understanding of the molecular mechanisms is not required in order to practice the present invention, because the molecular mechanisms mediating bacterial phagocytosis and killing are quite similar in neutrophils and macrophages and strong evidence exists implicating roles for the 5-LO pathway in functions of both cell types, studies are performed in both alveolar macrophages and glycogen-elicited peritoneal neutrophils from mice (purity of both populations exceeds 90%). Of note, neutrophil recruitment to the peritoneum following glycogen elicitation has been shown not to be impaired in 5-LO knockout mice. [X. Chen et al., Nature 372:179–182 (1994)]. Elicited neutrophils are studied instead of peripheral blood neutrophils because of the possibility that the process of recruitment and/or residence in an inflammatory milieu itself alters cellular phenotype. In addition, cells obtained from both wild type and knockout mice are studied.

Specifically, $10^5$ cells are coincubated for 1 hour with bacteria and lipids in the presence of 5% immune serum, and phagocytic index and bactericidal activity are assessed as described above under General Methods. In each experiment, a vehicle control is included. The exogenous 5-LO metabolites to be studied (all at $10^{-11}$–$10^{-7}$M) are i) $LTB_4$, ii) $LTC_4$; and iii) 5-HETE. Combinations of these lipids are also evaluated.

For 5-LO products that have stimulatory effects on phagocytosis or killing, the ability of specific receptor antagonists (described in Example 7) to abrogate these effects are also tested. All studies are carried out with both neutrophils and alveolar macrophages in order to ensure that instances in which a given compound exerts different effects on phagocytosis in the two cell types and exerts similar effects (though mediated by different mechanisms) in the two cell types are identified. Once a molecular mechanism for an effect on phagocytosis is identified (e.g., by $LTB_4$), the ability of the opposing compound (i.e., the $LTB_4$ receptor antagonist) to modulate that same molecular event in an opposite fashion is examined.

The mechanistic endpoints for study are as follows: i) surface expression of receptors necessary for binding/ingestion of K. pneumoniae (assessed by flow cytometry), including FcRII/FcRIII and CR3; ii) actin microfilament assembly (assessed by immunofluorescent staining and flow cytometry), necessary for particle engulfment; and iii) phagosome-lysosome fusion (assessed by acridine orange staining), necessary to bring the microbe in contact with the bactericidal arsenal. The General Methods describes the procedures for each of these assessments.

Bactericidal mechanisms are examined in a manner similar to that described for phagocytosis. Again, while an understanding of the molecular mechanisms is not required in order to practice the present invention, subsequent experiments are performed to address the molecular mechanism(s) that are responsible for 5-LO metabolites that augment killing of K. pneumoniae. Moreover, the ability of antagonists to block the positive effects of lipids on these mechanistic events are evaluated, and alveolar macrophages and elicited neutrophils are both studied. Three bactericidal mechanisms are examined (as described in the General Methods section). First, extracellular generation of $O_2$- is assessed by the superoxide dismutase-inhibitable reduction of ferricytochrome C. [L. Laichalk et al., FEMS Immunol. Med. Microbiol. 658:1–7 (1996)]. Because bacteria may not represent a sufficiently strong stimulus for extracellular release of oxygen metabolites, the effects of leukotrienes on this endpoint are also assessed using phorbol myristate acetate as the stimulus for $O_2$-production. Second, production of NO is determined by quantitating nitrite in culture medium using the Griess reagent. Third, release of a lysosomal enzyme, β-glucuronidase, is determined spectrophotometrically. [W. Hsueh et al., Exp. Lung Res. 13:385–399 (1987)].

Following characterization of the effects of exogenous leukotrienes on these molecular mechanisms in knockout as well as wild type cells, it is determined whether specific antagonism of these same leukotrienes produced endogenously has the same effects. As in Example 7, the $LTB_4$ antagonist CP-105,696 and the cysteinyl leukotriene antagonist MK-571 (both at $10^{-9}$–$10^{-6}$M) are used. They are added to wild type cells prior to addition of K. pneumoniae, and phagocytosis, killing, and relevant molecular mechanisms are then evaluated as described above.

If $LTB_4$ and $LTC_4$ are shown to exert their effects via different mechanisms, the combination of the two might activate antibacterial functions in a manner that is additive or synergistic. Such a finding has important implications for possible therapeutic use of leukotrienes in the in vivo studies described in Example 10.

EXAMPLE 10

The Effects of Aerosolized or Intratracheal Leukotrienes Post-Klebsiella Challenge on Bacterial Clearance and Survival in Both Wild Type and 5-LO Knockout Mice The data obtained from the preceding examples provides, among other things, information regarding the time point in the host response at which the presence of particular leukotrienes is most critical. The experiments of this example use that information to rationally test the in vivo efficacy of exogenous leukotrienes, either singly or in combination, administered by different routes.

The initial experiments of this example involve animals whose endogenous capacity for leukotriene generation is impaired because of 5-LO gene disruption. Subsequent experiments test the efficacy of intrapulmonary leukotriene administration in wild type mice. Finally, in addition to the clinically relevant endpoints of bacterial clearance and survival, the experiments of this example investigate the utility of profiling a molecular consequence of leukotriene action (e.g., CR3 expression) on lavaged cells as a possible surrogate for predicting diminished (without exogenous leukotrienes) or enhanced (with exogenous leukotrienes) bacterial clearance and survival.

"Early" Administration of Leukotrienes

Because of the data previously described (see FIG. 10) and because leukotriene-deficient animals are expected to manifest the greatest increment in antimicrobial defense from administration of exogenous leukotrienes, 5-LO knockout mice are used for the first series of studies. Knockout mice are given 50 CFU of K. pneumoniae intratracheally together with $LTB_4$ in doses ranging from 1–20 ng per animal (6 ng was the dose utilized in the experiment corresponding to FIG. 10); a similar dose range of $LTC_4$ is also tested. Lung and plasma bacterial CFUs are determined at 1 day, and the results of these experiments are used to determine optimal doses of concomitantly administered $LTB_4$ and $LTC_4$. Next, the effects on in vivo bacterial clearance are definitively assessed from lung and plasma CFUs at both 1 and 3 days post inoculation, using n=10 knockout animals for each assessment time point per treatment group, as follows: i) vehicle control (bacteria only) is assessed at 1 day; ii) vehicle control is assessed at 3 days; iii) $LTB_4$ is assessed at 1 day; iv) $LTB_4$ is assessed at 3 days; v) $LTC_4$ is assessed at 1 day; vi) $LTC_4$ is assessed at 3 days; vii) $LTB_4$ +$LTC_4$ are assessed at 1 day; and viii) $LTB_4$ +$LTC_4$ are assessed at 3 days. For further comparison, wild type animals inoculated with bacteria alone are studied at both time points (groups ix) and x)). Because combinations of optimal doses of $LTC_4$ and $LTB_4$ might prove excessively pro-inflammatory, such combination therapy may require that the doses of each agent be scaled back.

The treatment regimen(s) that yield(s) the greatest improvement in bacterial clearance is then utilized in a survival experiment. Once again, knockout mice (n=10 animals per group) are inoculated with 50 CFU of K. pneumoniae alone or together with optimal doses of $LTB_4$, $LTC_4$, or both leukotrienes; survival is monitored over 14 days. Wild type mice inoculated with bacteria alone serve as another comparison group.

"Late" Administration of Leukotrienes

Since prior experiments indicate that the effects of an intratracheal dose of leukotriene are rapid in onset (e.g., within 1 hour) but relatively short-lived (e.g., less than 12 hours), then administering leukotriene(s) together with the bacterial inoculum should augment the bacterial clearance potential of the alveolar macrophage. Alternatively, administering leukotriene(s) at a later time point is associated with other potential merits. For example, activation of the recruited neutrophils might be accomplished if active compound is dispensed at approximately 1–3 days post-inoculation. Moreover, an efficacious post-inoculation regimen is more readily applicable to treatment of overwhelming Gram-negative pneumonia in patients.

In light of the above, experiments are performed to define optimal time points (1, 2, and 3 days post-Klebsiella challenge) for "late" administration of $LTB_4$ and $LTC_4$. These are carried out in knockout mice and bacterial clearance (lung and plasma CFUs) are assessed at day 4; leukotriene-treated animals are then compared to no-leukotriene (vehicle) controls. Following determination of the best "late" time point, lung and plasma CFUs are determined 1 day thereafter in the following groups: i) bacteria alone, ii) bacteria+$LTB_4$, iii) bacteria+$LTC_4$, and iv) bacteria +$LTB_4$ +$LTC_4$ (n=10 animals per group). For further comparison, wild type animals inoculated with bacteria alone are studied. As described for the simultaneous treatment regimen, the optimal late treatment regimen is next tested in knockout mice in a 14 day survival study, with vehicle-treated knockout mice and wild type mice serving as comparison groups.

Simultaneous "Early" and "Late" Administration of Leukotrienes

Repeated or prolonged administration of leukotrienes may augment antibacterial host defense to a greater degree than either early or late administration alone. As a result, two additional regimens are performed. For both of these alternative regimens, 5-LO knockout mice are utilized, and bacterial clearance experiments are carried out first and optimal regimens are subsequently tested in longer survival experiments. The first regimen entails early (e.g., with inoculation) and late (e.g., day 2) administration. The early and late 5-LO metabolite can be selected independent of each other; in other words, $LTB_4$ can be utilized for one dose and $LTC_4$ for the other dose. The second regimen entails continuous administration of leukotriene(s) by aerosol. To ensure dosing limited to the respiratory tract and to be able to precisely quantitate the dose administered, leukotrienes are nebulized and administered to mice via a nose-only exposure chamber. Selection of the metabolite and the treatment window (e.g., days 1–3) is based on the results from the one-time dosing experiments.

Application to *K. pneumoniae*-challenged wild type mice

The experiments set forth above regarding leukotriene-deficient mice are applied to *K. pneumoniae*-challenged wild type mice. 129/SvEv wild type mice are more susceptible to Klebsiella pneumonia than are many other strains, although not as susceptible as 5-LO knockout mice. These wild type mice may therefore be more closely representative of patients susceptible to Gram-negative pneumonia than are the leukotriene-deficient animals. Therefore, the optimal leukotriene treatment strategy defined from studies in knockout mice is used in wild type mice, with similar endpoints of bacterial clearance and survival.

The experiments disclosed in this example indicate the effects of aerosolized and intratracheal administration of post-Klebsiella challenge on bacterial clearance and survival in both wild type and 5-LO knockout mice. These experiments serve to provide information regarding the in vivo administration of exogenous leukotrienes. The studies described involve treatment with leukotrienes $B_4$ and $C_4$; these were selected because of their known actions and their potency. However, the use of other 5-LO products, including 5-HETE and lipoxins is contemplated by the present invention.

It is to be understood that the invention is not to be limited to the exact details of operation or exact compounds, composition, methods, or procedures shown and described, as modifications and equivalents will be apparent to one skilled in the art.

We claim:

1. A method of enhancing antimicrobial defense, comprising administering an effective amount of a therapeutic composition to a host suspected of having a microbial infection, said composition comprising a cysteinyl leukotriene.

2. The method of claim 1, wherein said microbial infection is bacterial pneumonia.

3. The method of claim 1, wherein said cysteinyl leukotriene is selected from the group consisting of leukotriene $C_4$, leukotriene $D_4$ and leukotriene $E_4$.

4. A method of enhancing antimicrobial defense, comprising pulmonary administration of an effective amount of a therapeutic composition to an immunocompromised host, said composition comprising leukotriene $B_4$.

5. The method of claim 4, wherein said pulmonary administration is by aerosolization of said therapeutic composition.

6. The method of claim 1, further comprising the co-administration of an antibiotic to said host.

7. The method of claim 1, wherein said host is an animal.

8. The method of claim 1, wherein said host is a human.

9. A method of treating a bacterial infection, comprising pulmonary administration of an effective amount of a therapeutic composition to a host suspected of having a bacterial infection, said therapeutic composition comprising leukotriene $B_4$.

10. The method of claim 9, wherein said bacterial infection is bacterial pneumonia.

11. The method of claim 9, wherein said pulmonary administration is by aerosolization of said therapeutic composition.

12. The method of claim 11, further comprising the co-administration of an antibiotic to said host.

13. The method of claim 9, wherein said host is an animal.

14. The method of claim 9, wherein said host is a human.

* * * * *